(12) United States Patent
Raming et al.

(10) Patent No.: US 6,794,149 B1
(45) Date of Patent: Sep. 21, 2004

(54) GABA B RECEPTORS

(75) Inventors: Klaus Raming, Leverkusen (DE); Mario Mezler, Leverkusen (DE); Thomas Müller, Bonn (DE)

(73) Assignee: Bayer Aktiengesellschaft, Leverkusen (DE)

(*) Notice: Subject to any disclaimer, the term of this patent is extended or adjusted under 35 U.S.C. 154(b) by 0 days.

(21) Appl. No.: 09/715,962

(22) Filed: Nov. 17, 2000

(30) Foreign Application Priority Data

Nov. 18, 1999 (DE) .......................... 199 55 408

(51) Int. Cl.⁷ .................. G01N 33/566; C07K 1/00; C07H 21/04; C12N 1/20; C12P 21/06
(52) U.S. Cl. .................. 435/7.21; 435/7.2; 435/6; 435/69.5; 435/252.3; 435/320.1; 436/501; 514/2; 530/350
(58) Field of Search .................. 435/6, 7.2, 7.21, 435/69.5, 252.3, 320.1; 436/501; 514/2; 530/350

(56) References Cited

PUBLICATIONS

Bowie et al., 1990, Science 247:1306–1310.*
Alexander et al., Proc. Natl. Acad. Sci. 89(3352–3356)1992.*
Nature, vol. 363, May 20, 1993, pp. 274–276, Conklin et al, "Substitution of three amino acids switches receptor specificity of $G_q\alpha$ to that of $G_i\alpha$".
Nucleic Acids Research, vol. 12, No. 1, (month unavailable) 1984, pp. 387–395, Devereux et al, "A comprehensive set of sequence analysis programs for the VAX".
J. Morphol., vol. 136, 1972, pp. 153–180, J. N. Dumont, "Oogenesis in *Xenopus laevis* (Daudin), I. Stages of oocyte development in laboratory maintained animals[1]".
Comp. Biochem. And Physiol. Part C, vol. 122, 1999, pp. 283–286, A. Fukunaga et al, "Insecticidal properties 3–aminopropyl(methyl)phosphinic acid in its effect on $K^+$–evoked release of acetylcholine from cockroach synaptosomes".
Proc, Natl. Acad. Sci USA, vol. 88, Aug. 1991, pp. 7209–7213, R. H. Ffrench–Constant et al, "Molecular cloning and transformation of cyclodiene resistance in Drosophila: An invertebrate γ–aminobutyric acid subtype A receptor locus".
Pflügers Arch, vol. 391, 1981, pp. 85–100, O.P. Hamill, "Improved Patch–Clamp Techniques for High–Resolution Current Recording from Cells and Cell–free Membrane Patches".

(List continued on next page.)

Primary Examiner—Yvonne Eyler
Assistant Examiner—Michael Brannock
(74) Attorney, Agent, or Firm—Raymond J. Harmuth; Joseph C. Gil; John E. Mrozinski, Jr.

(57) ABSTRACT

The invention relates to polypeptides which exert the biological activity of GABA B receptors, and to nucleic acids which encode these polypeptides, and in particular to their use for finding active compounds for crop protection.

1 Claim, 2 Drawing Sheets

OTHER PUBLICATIONS

J. Neurochem., vol. 62, No. 6, 1994, pp. 2480–2483, R. J. Harvey et al, "Sequence of a Drosophila Ligand–Gated Ion–Channel Polypeptide with an Unusual Amino–Terminal Extracellular Domain".

Proc. Natl. Acad. Sci. USA, vol. 94, May, 1997, pp. 5195–5200, B. A. Hay, et al, "P element insertion–dependent gene activation in the Drosophila eye".

Biochem. Biophys. Res. Commun., vol. 193, No. 2, Jun. 15, 1993, pp. 474–482, J. E. Henderson, et al, "Characterization of a putative γ–aminobutyric acid (GABA) receptor β subunit gene from *Drosophila melanogaster*".

Nature, vol. 396, Dec. 17, 1998, pp. 674–679, K. A. Jones et al, "$GABA_B$receptors function as a heteromeric assembly of the subunits $GABA_BR1$ and $GABA_BR2$".

Nature, vol. 396, Dec 17, 1998, pp. 683–687, K. Kaupmann et al, "$GABA_B$–receptor subtypes assemble into functional heteromeric complexes".

Transposable Elements/Current Topics in Microbiology and Immunology, vol. 204, (month unavilable), 1996, Plasterk, "The Tc1/mariner Transposon Family".

Analytical Biochemistry, vol. 252, 1997, pp. 115–126, J. Stables et al, "A Bioluminescent Assay for Agonist Activity at Potentially Any G–Protein–Coupled Receptor".

Current Opinion in Biotechnology, vol. 6, 1995, pp. 574–581, C. Stratowa et al, "Use of a luciferase reporter system for characterizing G–protein–linked receptors".

\* cited by examiner

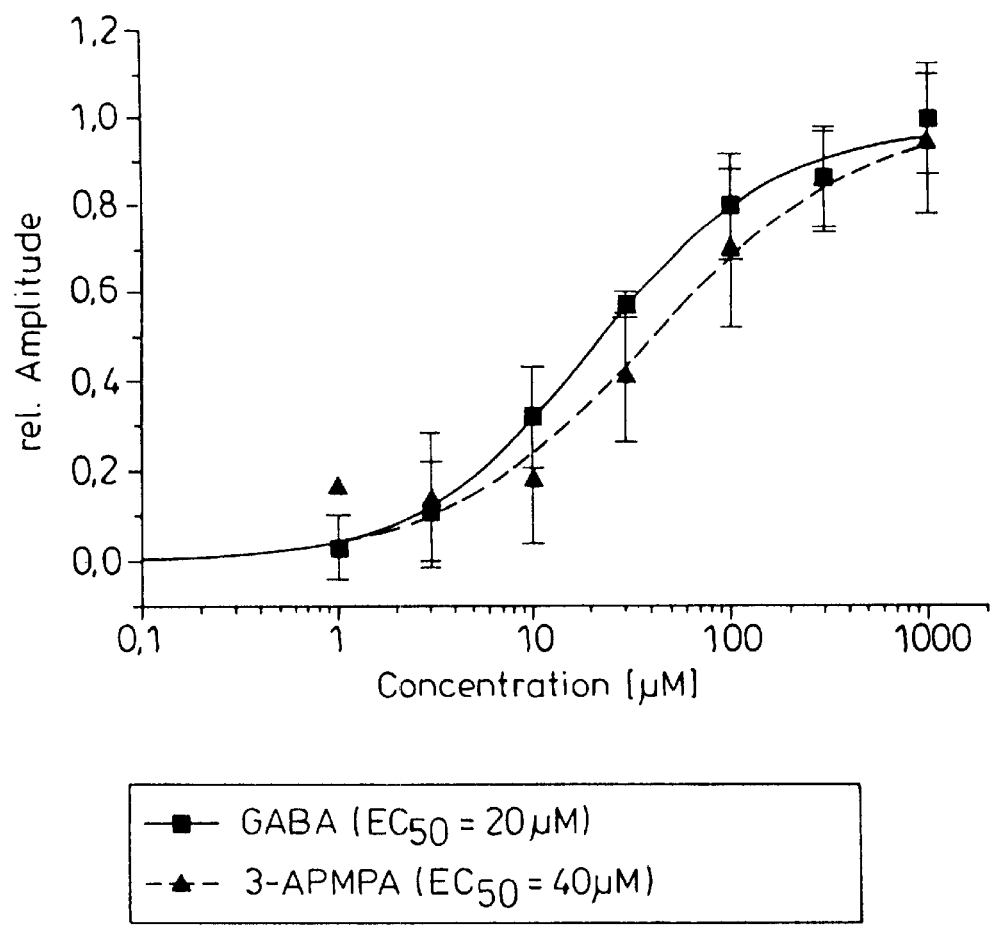

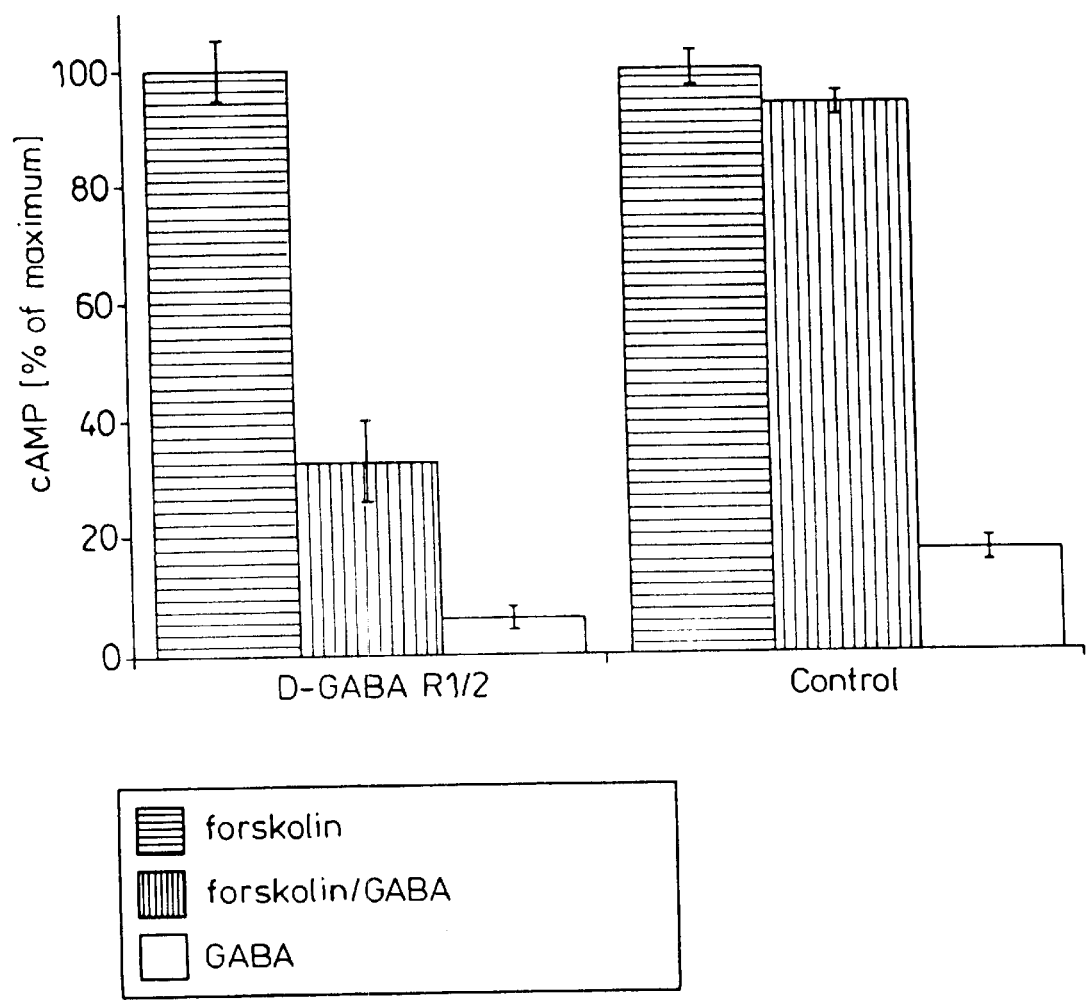

SEQUENCE LISTING

```
<160> NUMBER OF SEQ ID NOS:  6

<210> SEQ ID NO 1
<211> LENGTH: 2523
<212> TYPE: DNA
<213> ORGANISM: Drosophila melanogaster
<220> FEATURE:
<221> NAME/KEY: CDS
<222> LOCATION: (1)..(2520)

<400> SEQUENCE: 1 atg cgc aaa gat atg aca agt gat ggt gct gtt acg ttt tgg ata ttt        48
Met Arg Lys Asp Met Thr Ser Asp Gly Ala Val Thr Phe Trp Ile Phe
  1               5                  10                  15 ttg ctt tgt tta atc gcc tcg ccg cac ctg caa ggg ggc gtg gcc ggg        96
Leu Leu Cys Leu Ile Ala Ser Pro His Leu Gln Gly Gly Val Ala Gly
             20                  25                  30 agg ccc gat gaa ctg cac atc ggc ggc atc ttt ccg ata gcc ggc aaa       144
```

-continued

| | | |
|---|---|---|
| Arg Pro Asp Glu Leu His Ile Gly Gly Ile Phe Pro Ile Ala Gly Lys<br>35 40 45 | | |
| gga gga tgg cag ggc ggc cag gcg tgt atg cct gcc aca aga ctg gcg<br>Gly Gly Trp Gln Gly Gly Gln Ala Cys Met Pro Ala Thr Arg Leu Ala<br>50 55 60 | 192 | |
| ttg gat gat gtc aac aag cag ccg aat ctg ctg ccg ggc ttc aag ctc<br>Leu Asp Asp Val Asn Lys Gln Pro Asn Leu Leu Pro Gly Phe Lys Leu<br>65 70 75 80 | 240 | |
| atc ctg cac agc aac gac agc gag tgt gag ccc ggt ttg ggc gcc agc<br>Ile Leu His Ser Asn Asp Ser Glu Cys Glu Pro Gly Leu Gly Ala Ser<br>85 90 95 | 288 | |
| gtg atg tac aat ctg ctc tat aat aaa ccg caa aag ctg atg ctg ttg<br>Val Met Tyr Asn Leu Leu Tyr Asn Lys Pro Gln Lys Leu Met Leu Leu<br>100 105 110 | 336 | |
| gca gga tgc agc acg gtc tgc acc act gta gcc gag gct gcc aaa atg<br>Ala Gly Cys Ser Thr Val Cys Thr Thr Val Ala Glu Ala Ala Lys Met<br>115 120 125 | 384 | |
| tgg aat cta att gtg ctc tgc tac ggg gcc tcg agt ccg gct ctt tcg<br>Trp Asn Leu Ile Val Leu Cys Tyr Gly Ala Ser Ser Pro Ala Leu Ser<br>130 135 140 | 432 | |
| gat cgc aaa cga ttc ccc act cta ttc cgc acc cat cca tcg gcc acg<br>Asp Arg Lys Arg Phe Pro Thr Leu Phe Arg Thr His Pro Ser Ala Thr<br>145 150 155 160 | 480 | |
| gtg cac aat cca acg cgc atc aag ctg atg aag aaa ttc ggc tgg tcc<br>Val His Asn Pro Thr Arg Ile Lys Leu Met Lys Lys Phe Gly Trp Ser<br>165 170 175 | 528 | |
| cgg gtg gcc att ctg cag cag gcg gag gag gtc ttt ata tcg acc gta<br>Arg Val Ala Ile Leu Gln Gln Ala Glu Glu Val Phe Ile Ser Thr Val<br>180 185 190 | 576 | |
| gag gat ctc gag aat cga tgc atg gag gct ggc gtt gaa atc gta act<br>Glu Asp Leu Glu Asn Arg Cys Met Glu Ala Gly Val Glu Ile Val Thr<br>195 200 205 | 624 | |
| aga caa tca ttt cta tcc gat cca aca gac gcc gtg cgc aat ttg cga<br>Arg Gln Ser Phe Leu Ser Asp Pro Thr Asp Ala Val Arg Asn Leu Arg<br>210 215 220 | 672 | |
| cgc cag gat gca cgc atc att gtg gga ctc ttc tat gtg gtg gcc gcc<br>Arg Gln Asp Ala Arg Ile Ile Val Gly Leu Phe Tyr Val Val Ala Ala<br>225 230 235 240 | 720 | |
| agg agg gtg ctc tgc gaa atg tac aaa cag cag cta tat ggc cga gct<br>Arg Arg Val Leu Cys Glu Met Tyr Lys Gln Gln Leu Tyr Gly Arg Ala<br>245 250 255 | 768 | |
| cat gtg tgg ttc ttt att ggc tgg tac gag gac aac tgg tac gag gtg<br>His Val Trp Phe Phe Ile Gly Trp Tyr Glu Asp Asn Trp Tyr Glu Val<br>260 265 270 | 816 | |
| aat ctg aaa gca gag ggc atc acc tgc act gtt gaa cag atg cga ata<br>Asn Leu Lys Ala Glu Gly Ile Thr Cys Thr Val Glu Gln Met Arg Ile<br>275 280 285 | 864 | |
| gct gcc gaa gga cat ctg aca acg gaa gcg ctc atg tgg aat cag aac<br>Ala Ala Glu Gly His Leu Thr Thr Glu Ala Leu Met Trp Asn Gln Asn<br>290 295 300 | 912 | |
| aat cag aca act ata tcc gga atg act gca gag gaa ttt cga cat cga<br>Asn Gln Thr Thr Ile Ser Gly Met Thr Ala Glu Glu Phe Arg His Arg<br>305 310 315 320 | 960 | |
| ctg aat cag gcg cta atc gag gag ggt tac gac att aac cac gat cgc<br>Leu Asn Gln Ala Leu Ile Glu Glu Gly Tyr Asp Ile Asn His Asp Arg<br>325 330 335 | 1008 | |
| tat ccg gag gga tat cag gag gcg cca ctc gcc tac gat gca gtg tgg<br>Tyr Pro Glu Gly Tyr Gln Glu Ala Pro Leu Ala Tyr Asp Ala Val Trp<br>340 345 350 | 1056 | |

```
                                                                -continued agt gtg gct ttg gct ttc aac aag acc atg gaa cga ttg aca acc ggg       1104
Ser Val Ala Leu Ala Phe Asn Lys Thr Met Glu Arg Leu Thr Thr Gly
        355                 360                 365 aag aaa tct ctg agg gat ttt acc tat acg gac aag gag att gcc gat       1152
Lys Lys Ser Leu Arg Asp Phe Thr Tyr Thr Asp Lys Glu Ile Ala Asp
    370                 375                 380 gaa atc tac gct gcc atg aac tcc aca caa ttt ctg ggt gta tcg ggt       1200
Glu Ile Tyr Ala Ala Met Asn Ser Thr Gln Phe Leu Gly Val Ser Gly
385                 390                 395                 400 gtg gtg gca ttc agt tct cag ggc gat cgt att gct ctt aca cag atc       1248
Val Val Ala Phe Ser Ser Gln Gly Asp Arg Ile Ala Leu Thr Gln Ile
                405                 410                 415 gaa cag atg ata gac ggc aag tac gag aag ttg ggt tac tac gat act       1296
Glu Gln Met Ile Asp Gly Lys Tyr Glu Lys Leu Gly Tyr Tyr Asp Thr
        420                 425                 430 cag ttg gat aac cta tcc tgg ttg aat act gaa cag tgg att ggt ggc       1344
Gln Leu Asp Asn Leu Ser Trp Leu Asn Thr Glu Gln Trp Ile Gly Gly
    435                 440                 445 aag gtt cct caa gat cgc aca att gtc acc cat gtt cta cgc acc gtg       1392
Lys Val Pro Gln Asp Arg Thr Ile Val Thr His Val Leu Arg Thr Val
450                 455                 460 tcc ttg cca tta ttt gtg tgc atg tgc aca ata tcc agt tgt ggc ata       1440
Ser Leu Pro Leu Phe Val Cys Met Cys Thr Ile Ser Ser Cys Gly Ile
465                 470                 475                 480 ttc gtt gcc ttc gcc ttg atc atc ttt aat ata tgg aat aag cat aga       1488
Phe Val Ala Phe Ala Leu Ile Ile Phe Asn Ile Trp Asn Lys His Arg
                485                 490                 495 aga gta ata caa tcc tcg cat ccc gtt tgc aat acg atc atg tta ttt       1536
Arg Val Ile Gln Ser Ser His Pro Val Cys Asn Thr Ile Met Leu Phe
        500                 505                 510 ggt gtc atc atc tgt cta ata tct gtc atc tta ctg ggc atc gac gga       1584
Gly Val Ile Ile Cys Leu Ile Ser Val Ile Leu Leu Gly Ile Asp Gly
    515                 520                 525 cgc ttt gtc agc ccc gag gaa tat cca aag ata tgt caa gcg cgg gct       1632
Arg Phe Val Ser Pro Glu Glu Tyr Pro Lys Ile Cys Gln Ala Arg Ala
530                 535                 540 tgg tta cta tcc acc ggt ttt aca cta gca tac ggt gct atg ttc agc       1680
Trp Leu Leu Ser Thr Gly Phe Thr Leu Ala Tyr Gly Ala Met Phe Ser
545                 550                 555                 560 aag gtc tgg cgt gtg cat cgt ttt aca aca aaa gca aaa act gac cca       1728
Lys Val Trp Arg Val His Arg Phe Thr Thr Lys Ala Lys Thr Asp Pro
                565                 570                 575 aag aaa aaa gtg gaa cct tgg aag cta tac acc atg gtt tcg ggg cta       1776
Lys Lys Lys Val Glu Pro Trp Lys Leu Tyr Thr Met Val Ser Gly Leu
        580                 585                 590 tta tca ata gat tta gtg ata tta ctc tca tgg cag atc ttt gat ccg       1824
Leu Ser Ile Asp Leu Val Ile Leu Leu Ser Trp Gln Ile Phe Asp Pro
    595                 600                 605 ctg cag cgt tat ctc gaa aca ttc cca ctc gaa gat cca gta tct act       1872
Leu Gln Arg Tyr Leu Glu Thr Phe Pro Leu Glu Asp Pro Val Ser Thr
610                 615                 620 act gat gat att aaa ata cgt cca gag ctt gag cat tgt gaa agt caa       1920
Thr Asp Asp Ile Lys Ile Arg Pro Glu Leu Glu His Cys Glu Ser Gln
625                 630                 635                 640 cgc aac tcc atg tgg ttg ggt ctt gta tac ggc ttc aag ggg cta atc       1968
Arg Asn Ser Met Trp Leu Gly Leu Val Tyr Gly Phe Lys Gly Leu Ile
                645                 650                 655 ctg gtg ttt ggc ctc ttt ttg gcg tac gag acg cgc tcc att aaa gtg       2016
Leu Val Phe Gly Leu Phe Leu Ala Tyr Glu Thr Arg Ser Ile Lys Val
        660                 665                 670
```

-continued

```
aaa cag atc aac gat tcg cgt tat gtg ggc atg agc atc tat aac gtg    2064
Lys Gln Ile Asn Asp Ser Arg Tyr Val Gly Met Ser Ile Tyr Asn Val
            675                 680                 685 gtc gtc ctt tgc ctg ata aca gct ccg gtg ggc atg gtc att gca tcg    2112
Val Val Leu Cys Leu Ile Thr Ala Pro Val Gly Met Val Ile Ala Ser
        690                 695                 700 caa cag gac gcg tcc ttt gcc ttc gtt gct cta gct gtg ata ttc tgt    2160
Gln Gln Asp Ala Ser Phe Ala Phe Val Ala Leu Ala Val Ile Phe Cys
705                 710                 715                 720 tgt ttc cta agc atg ctg ctg ata ttt gtg cca aag gtc att gag gtt    2208
Cys Phe Leu Ser Met Leu Leu Ile Phe Val Pro Lys Val Ile Glu Val
                725                 730                 735 ata cgt cat ccc aag gat aag gcc gaa tcg aaa tac aat ccc gat tca    2256
Ile Arg His Pro Lys Asp Lys Ala Glu Ser Lys Tyr Asn Pro Asp Ser
            740                 745                 750 gcc ata tcg aaa gag gac gaa gaa cgc tat cag aaa ctt gtt acc gaa    2304
Ala Ile Ser Lys Glu Asp Glu Glu Arg Tyr Gln Lys Leu Val Thr Glu
        755                 760                 765 aac gag caa ttg caa cga tta ata aca cag aag gag gaa aag att cga    2352
Asn Glu Gln Leu Gln Arg Leu Ile Thr Gln Lys Glu Glu Lys Ile Arg
770                 775                 780 gtc ctg cga cag cgt ctg gtg gag cgg ggc gac gcc aag ggc aca gaa    2400
Val Leu Arg Gln Arg Leu Val Glu Arg Gly Asp Ala Lys Gly Thr Glu
785                 790                 795                 800 ctg aat ggt gca aca ggt gtc gcc tcc gcc gcc gtt gca aca act tcg    2448
Leu Asn Gly Ala Thr Gly Val Ala Ser Ala Ala Val Ala Thr Thr Ser
                805                 810                 815 cag ccc gct tcc ctc atc aac tca tca gca cat gcc acg ccc gca gcc    2496
Gln Pro Ala Ser Leu Ile Asn Ser Ser Ala His Ala Thr Pro Ala Ala
            820                 825                 830 aca ctc gca atc aca caa ggt gag tag                                2523
Thr Leu Ala Ile Thr Gln Gly Glu
        835                 840

<210> SEQ ID NO 2
<211> LENGTH: 840
<212> TYPE: PRT
<213> ORGANISM: Drosophila melanogaster

<400> SEQUENCE: 2

Met Arg Lys Asp Met Thr Ser Asp Gly Ala Val Thr Phe Trp Ile Phe
1               5                   10                  15

Leu Leu Cys Leu Ile Ala Ser Pro His Leu Gln Gly Gly Val Ala Gly
            20                  25                  30

Arg Pro Asp Glu Leu His Ile Gly Gly Ile Phe Pro Ile Ala Gly Lys
        35                  40                  45

Gly Gly Trp Gln Gly Gly Gln Ala Cys Met Pro Ala Thr Arg Leu Ala
    50                  55                  60

Leu Asp Asp Val Asn Lys Gln Pro Asn Leu Leu Pro Gly Phe Lys Leu
65                  70                  75                  80

Ile Leu His Ser Asn Asp Ser Glu Cys Glu Pro Gly Leu Gly Ala Ser
                85                  90                  95

Val Met Tyr Asn Leu Leu Tyr Asn Lys Pro Gln Lys Leu Met Leu Leu
            100                 105                 110

Ala Gly Cys Ser Thr Val Cys Thr Thr Val Ala Glu Ala Ala Lys Met
        115                 120                 125

Trp Asn Leu Ile Val Leu Cys Tyr Gly Ala Ser Ser Pro Ala Leu Ser
    130                 135                 140
```

-continued

```
Asp Arg Lys Arg Phe Pro Thr Leu Phe Arg Thr His Pro Ser Ala Thr
145                 150                 155                 160

Val His Asn Pro Thr Arg Ile Lys Leu Met Lys Lys Phe Gly Trp Ser
                165                 170                 175

Arg Val Ala Ile Leu Gln Gln Ala Glu Val Phe Ile Ser Thr Val
            180                 185                 190

Glu Asp Leu Glu Asn Arg Cys Met Glu Ala Gly Val Glu Ile Val Thr
            195                 200                 205

Arg Gln Ser Phe Leu Ser Asp Pro Thr Asp Ala Val Arg Asn Leu Arg
    210                 215                 220

Arg Gln Asp Ala Arg Ile Ile Val Gly Leu Phe Tyr Val Val Ala Ala
225                 230                 235                 240

Arg Arg Val Leu Cys Glu Met Tyr Lys Gln Gln Leu Tyr Gly Arg Ala
                245                 250                 255

His Val Trp Phe Phe Ile Gly Trp Tyr Glu Asp Asn Trp Tyr Glu Val
                260                 265                 270

Asn Leu Lys Ala Glu Gly Ile Thr Cys Thr Val Glu Gln Met Arg Ile
            275                 280                 285

Ala Ala Glu Gly His Leu Thr Thr Glu Ala Leu Met Trp Asn Gln Asn
290                 295                 300

Asn Gln Thr Thr Ile Ser Gly Met Thr Ala Glu Glu Phe Arg His Arg
305                 310                 315                 320

Leu Asn Gln Ala Leu Ile Glu Glu Gly Tyr Asp Ile Asn His Asp Arg
            325                 330                 335

Tyr Pro Glu Gly Tyr Gln Glu Ala Pro Leu Ala Tyr Asp Ala Val Trp
            340                 345                 350

Ser Val Ala Leu Ala Phe Asn Lys Thr Met Glu Arg Leu Thr Thr Gly
            355                 360                 365

Lys Lys Ser Leu Arg Asp Phe Thr Tyr Thr Asp Lys Glu Ile Ala Asp
    370                 375                 380

Glu Ile Tyr Ala Ala Met Asn Ser Thr Gln Phe Leu Gly Val Ser Gly
385                 390                 395                 400

Val Val Ala Phe Ser Ser Gln Gly Asp Arg Ile Ala Leu Thr Gln Ile
            405                 410                 415

Glu Gln Met Ile Asp Gly Lys Tyr Glu Lys Leu Gly Tyr Tyr Asp Thr
            420                 425                 430

Gln Leu Asp Asn Leu Ser Trp Leu Asn Thr Glu Gln Trp Ile Gly Gly
    435                 440                 445

Lys Val Pro Gln Asp Arg Thr Ile Val Thr His Val Leu Arg Thr Val
    450                 455                 460

Ser Leu Pro Leu Phe Val Cys Met Cys Thr Ile Ser Ser Cys Gly Ile
465                 470                 475                 480

Phe Val Ala Phe Ala Leu Ile Ile Phe Asn Ile Trp Asn Lys His Arg
            485                 490                 495

Arg Val Ile Gln Ser Ser His Pro Val Cys Asn Thr Ile Met Leu Phe
                500                 505                 510

Gly Val Ile Ile Cys Leu Ile Ser Val Ile Leu Leu Gly Ile Asp Gly
            515                 520                 525

Arg Phe Val Ser Pro Glu Glu Tyr Pro Lys Ile Cys Gln Ala Arg Ala
    530                 535                 540

Trp Leu Leu Ser Thr Gly Phe Thr Leu Ala Tyr Gly Ala Met Phe Ser
545                 550                 555                 560
```

-continued

```
Lys Val Trp Arg Val His Arg Phe Thr Thr Lys Ala Lys Thr Asp Pro
                565                 570                 575

Lys Lys Lys Val Glu Pro Trp Lys Leu Tyr Thr Met Val Ser Gly Leu
            580                 585                 590

Leu Ser Ile Asp Leu Val Ile Leu Ser Trp Gln Ile Phe Asp Pro
        595                 600                 605

Leu Gln Arg Tyr Leu Glu Thr Phe Pro Leu Glu Asp Pro Val Ser Thr
    610                 615                 620

Thr Asp Asp Ile Lys Ile Arg Pro Glu Leu Glu His Cys Glu Ser Gln
625                 630                 635                 640

Arg Asn Ser Met Trp Leu Gly Leu Val Tyr Gly Phe Lys Gly Leu Ile
                645                 650                 655

Leu Val Phe Gly Leu Phe Leu Ala Tyr Glu Thr Arg Ser Ile Lys Val
            660                 665                 670

Lys Gln Ile Asn Asp Ser Arg Tyr Val Gly Met Ser Ile Tyr Asn Val
        675                 680                 685

Val Val Leu Cys Leu Ile Thr Ala Pro Val Gly Met Val Ile Ala Ser
    690                 695                 700

Gln Gln Asp Ala Ser Phe Ala Phe Val Ala Leu Ala Val Ile Phe Cys
705                 710                 715                 720

Cys Phe Leu Ser Met Leu Leu Ile Phe Val Pro Lys Val Ile Glu Val
                725                 730                 735

Ile Arg His Pro Lys Asp Lys Ala Glu Ser Lys Tyr Asn Pro Asp Ser
            740                 745                 750

Ala Ile Ser Lys Glu Asp Glu Glu Arg Tyr Gln Lys Leu Val Thr Glu
        755                 760                 765

Asn Glu Gln Leu Gln Arg Leu Ile Thr Gln Lys Glu Glu Lys Ile Arg
    770                 775                 780

Val Leu Arg Gln Arg Leu Val Glu Arg Gly Asp Ala Lys Gly Thr Glu
785                 790                 795                 800

Leu Asn Gly Ala Thr Gly Val Ala Ser Ala Ala Val Ala Thr Thr Ser
                805                 810                 815

Gln Pro Ala Ser Leu Ile Asn Ser Ser Ala His Ala Thr Pro Ala Ala
            820                 825                 830

Thr Leu Ala Ile Thr Gln Gly Glu
        835                 840

<210> SEQ ID NO 3
<211> LENGTH: 3663
<212> TYPE: DNA
<213> ORGANISM: Drosophila melanogaster
<220> FEATURE:
<221> NAME/KEY: CDS
<222> LOCATION: (1)..(3660)

<400> SEQUENCE: 3 atg ttc cgg cca agt tgg ttt cca ttc gcc agc ctg ctg ttc ctg ctc    48
Met Phe Arg Pro Ser Trp Phe Pro Phe Ala Ser Leu Leu Phe Leu Leu
1               5                   10                  15 ctt tgg agc acc gcc tgt ggc agg aca gcc aag aga tcg gac gtc tac    96
Leu Trp Ser Thr Ala Cys Gly Arg Thr Ala Lys Arg Ser Asp Val Tyr
            20                  25                  30 ata gcg gga ttc ttc ccg tac ggg gat ggc gtg gaa aac tcc tac acc   144
Ile Ala Gly Phe Phe Pro Tyr Gly Asp Gly Val Glu Asn Ser Tyr Thr
        35                  40                  45 ggt cgg ggc gtt atg ccc agt gta aag ctc gcc ttg ggt cac gtt aat   192
Gly Arg Gly Val Met Pro Ser Val Lys Leu Ala Leu Gly His Val Asn
```

-continued

```
              50                  55                  60
gag cat gga aag ata ctg gcc aac tac agg ctg cac atg tgg tgg aac       240
Glu His Gly Lys Ile Leu Ala Asn Tyr Arg Leu His Met Trp Trp Asn
 65                  70                  75                  80 gac act cag tgc aat gct gct gtg ggc gta aag tcc ttc ttc gat atg       288
Asp Thr Gln Cys Asn Ala Ala Val Gly Val Lys Ser Phe Phe Asp Met
                 85                  90                  95 atg cat tcg ggt ccc aat aaa gtg atg ctc ttc ggc gct gcg tgc acc       336
Met His Ser Gly Pro Asn Lys Val Met Leu Phe Gly Ala Ala Cys Thr
                100                 105                 110 cat gtg acc gat ccc ata gcc aag gcc agc aag cac tgg cac ctc acc       384
His Val Thr Asp Pro Ile Ala Lys Ala Ser Lys His Trp His Leu Thr
            115                 120                 125 cag ctc agc tac gcg gac acc cat ccc atg ttc acc aag gat gcg ttt       432
Gln Leu Ser Tyr Ala Asp Thr His Pro Met Phe Thr Lys Asp Ala Phe
        130                 135                 140 ccg aat ttc ttt cgc gtg gta ccc tcg gag aat gcc ttt aat gcg ccg       480
Pro Asn Phe Phe Arg Val Val Pro Ser Glu Asn Ala Phe Asn Ala Pro
145                 150                 155                 160 cga ctg gcc ttg ctg aag gag ttc aat tgg acc aga gtg ggc act gtc       528
Arg Leu Ala Leu Leu Lys Glu Phe Asn Trp Thr Arg Val Gly Thr Val
                165                 170                 175 tac cag aat gag cca cgc tat tcg ctg ccc cac aat cac atg gtg gct       576
Tyr Gln Asn Glu Pro Arg Tyr Ser Leu Pro His Asn His Met Val Ala
            180                 185                 190 gac ctg gat gcc atg gag gtc gag gtg gtg gaa acg cag agc ttc gtc       624
Asp Leu Asp Ala Met Glu Val Glu Val Val Glu Thr Gln Ser Phe Val
        195                 200                 205 aac gat gtg gct gaa tca ttg aag aaa ctg cgc gag aag gac gtg agg       672
Asn Asp Val Ala Glu Ser Leu Lys Lys Leu Arg Glu Lys Asp Val Arg
210                 215                 220 atc att ctg ggc aac ttt aac gag cac ttt gca cgc aag gca ttc tgt       720
Ile Ile Leu Gly Asn Phe Asn Glu His Phe Ala Arg Lys Ala Phe Cys
225                 230                 235                 240 gag gct tat aaa ttg gat atg tat ggc aga gcc tat caa tgg ctg atc       768
Glu Ala Tyr Lys Leu Asp Met Tyr Gly Arg Ala Tyr Gln Trp Leu Ile
                245                 250                 255 atg gct acc tat tcc acg gat tgg tgg aat gtc acg cag gac agc gag       816
Met Ala Thr Tyr Ser Thr Asp Trp Trp Asn Val Thr Gln Asp Ser Glu
            260                 265                 270 tgc agt gtg gag gag atc gct aca gcc ttg gaa ggt gcc att cta gtg       864
Cys Ser Val Glu Glu Ile Ala Thr Ala Leu Glu Gly Ala Ile Leu Val
        275                 280                 285 gat ctt ttg ccc ttg tcc acc agt ggt gac atc aca gtg gct ggc att       912
Asp Leu Leu Pro Leu Ser Thr Ser Gly Asp Ile Thr Val Ala Gly Ile
290                 295                 300 act gct gat gag tat ctt gtg gag tac gac aga ctg cga ggc act gaa       960
Thr Ala Asp Glu Tyr Leu Val Glu Tyr Asp Arg Leu Arg Gly Thr Glu
305                 310                 315                 320 tat tcc cgc ttt cat ggc tat acc tac gat ggt atc tgg gca gct gcc      1008
Tyr Ser Arg Phe His Gly Tyr Thr Tyr Asp Gly Ile Trp Ala Ala Ala
                325                 330                 335 ctg gcc att cag tat gtg gcc gaa aag cga gag gat ctg cta aca cat      1056
Leu Ala Ile Gln Tyr Val Ala Glu Lys Arg Glu Asp Leu Leu Thr His
            340                 345                 350 ttt gat tat cgc gtg aag gac tgg gag agt gtc ttc ctt gag gct cta      1104
Phe Asp Tyr Arg Val Lys Asp Trp Glu Ser Val Phe Leu Glu Ala Leu
        355                 360                 365 cgt aat aca tcc ttc gag ggt gtg acg gga ccc gtg cgt ttc tac aac      1152
```

```
                Arg Asn Thr Ser Phe Glu Gly Val Thr Gly Pro Val Arg Phe Tyr Asn
                    370                 375                 380 aac gag cgc aag gcc aac atc ctg atc aat cag ttt cag ctg gga caa           1200
Asn Glu Arg Lys Ala Asn Ile Leu Ile Asn Gln Phe Gln Leu Gly Gln
385                 390                 395                 400 atg gaa aag atc ggg gaa tac cac tca cag aag tca cac ttg gat tta           1248
Met Glu Lys Ile Gly Glu Tyr His Ser Gln Lys Ser His Leu Asp Leu
                405                 410                 415 agc ttg gga aaa cca gtc aaa tgg gtg ggg aaa act cct ccc aag gat           1296
Ser Leu Gly Lys Pro Val Lys Trp Val Gly Lys Thr Pro Pro Lys Asp
            420                 425                 430 cgc act ttg atc tac atc gag cac agt cag gtc aat cca acc ata tat           1344
Arg Thr Leu Ile Tyr Ile Glu His Ser Gln Val Asn Pro Thr Ile Tyr
        435                 440                 445 att gta tcg gct agt gct tcg gtc att gga gtg att att gcc aca gtt           1392
Ile Val Ser Ala Ser Ala Ser Val Ile Gly Val Ile Ile Ala Thr Val
    450                 455                 460 ttt ctg gcc ttt aac att aag tat cgc aat caa aga tac atc aag atg           1440
Phe Leu Ala Phe Asn Ile Lys Tyr Arg Asn Gln Arg Tyr Ile Lys Met
465                 470                 475                 480 tcc agt ccc cat ttg aac aat ctg atc att gtg ggc tgt atg att acc           1488
Ser Ser Pro His Leu Asn Asn Leu Ile Ile Val Gly Cys Met Ile Thr
                485                 490                 495 tat ttg agc atc att ttc ctg ggt ctc gat acc aca tta agt agt gtg           1536
Tyr Leu Ser Ile Ile Phe Leu Gly Leu Asp Thr Thr Leu Ser Ser Val
                500                 505                 510 gca gct ttt ccc tat atc tgc aca gct cga gcc tgg atc ttg atg gct           1584
Ala Ala Phe Pro Tyr Ile Cys Thr Ala Arg Ala Trp Ile Leu Met Ala
            515                 520                 525 gga ttc agt ctc agt ttt gga gcc atg ttc tcg aag acg tgg cgg gtg           1632
Gly Phe Ser Leu Ser Phe Gly Ala Met Phe Ser Lys Thr Trp Arg Val
        530                 535                 540 cat tcg ata ttc acc gat ctg aag ctc aat aag aag gtg atc aag gac           1680
His Ser Ile Phe Thr Asp Leu Lys Leu Asn Lys Lys Val Ile Lys Asp
545                 550                 555                 560 tat caa ttg ttt atg gtt gtg ggc gtg ctt ttg gcc att gat ata gcc           1728
Tyr Gln Leu Phe Met Val Val Gly Val Leu Leu Ala Ile Asp Ile Ala
                565                 570                 575 att ata acc acc tgg cag att gcc gat ccc ttt tac cgc gaa act aaa           1776
Ile Ile Thr Thr Trp Gln Ile Ala Asp Pro Phe Tyr Arg Glu Thr Lys
                580                 585                 590 cag ttg gaa ccc ttg cat cac gag aat att gat gat gtc ttg gtg atc           1824
Gln Leu Glu Pro Leu His His Glu Asn Ile Asp Asp Val Leu Val Ile
            595                 600                 605 ccc gaa aac gag tac tgc cag tct gag cac atg acc ata ttc gtt agc           1872
Pro Glu Asn Glu Tyr Cys Gln Ser Glu His Met Thr Ile Phe Val Ser
        610                 615                 620 att att tat gcc tac aag gga ctg ttg ttg gtt ttt ggc gcc ttt ttg           1920
Ile Ile Tyr Ala Tyr Lys Gly Leu Leu Leu Val Phe Gly Ala Phe Leu
625                 630                 635                 640 gcc tgg gaa act cga cat gtt tct ata ccg gct ctg aac gat tcc aag           1968
Ala Trp Glu Thr Arg His Val Ser Ile Pro Ala Leu Asn Asp Ser Lys
                645                 650                 655 cat att ggt ttc tcc gtt tat aac gtg ttc atc act tgt ctg gcc gga           2016
His Ile Gly Phe Ser Val Tyr Asn Val Phe Ile Thr Cys Leu Ala Gly
                660                 665                 670 gcg gct ata tcc ctg gtg cta tcg gat cga aag gat tta gtt ttt gtc           2064
Ala Ala Ile Ser Leu Val Leu Ser Asp Arg Lys Asp Leu Val Phe Val
            675                 680                 685
```

```
tta ctc tcg ttt ttt atc att ttt tgt acg aca gcc act ttg tgt ttg      2112
Leu Leu Ser Phe Phe Ile Ile Phe Cys Thr Thr Ala Thr Leu Cys Leu
        690             695                 700 gtg ttc gta ccg aaa ttg gtg gag ctg aag cgg aat ccc cag ggc gtg      2160
Val Phe Val Pro Lys Leu Val Glu Leu Lys Arg Asn Pro Gln Gly Val
705             710                 715                 720 gtg gac aaa cgc gtt agg gcc acg ttg aga ccc atg tcc aaa aac gga      2208
Val Asp Lys Arg Val Arg Ala Thr Leu Arg Pro Met Ser Lys Asn Gly
                725                 730                 735 cgc cgg gat tcc tcg gtg tgc gaa ctg gag caa cga ttg cga gat gta      2256
Arg Arg Asp Ser Ser Val Cys Glu Leu Glu Gln Arg Leu Arg Asp Val
            740                 745                 750 aag aac aca aac tgc cga ttc cga aag gcg ctg atg gag aag gag aac      2304
Lys Asn Thr Asn Cys Arg Phe Arg Lys Ala Leu Met Glu Lys Glu Asn
        755                 760                 765 gag ctg cag gcc tta atc cgc aag ctg gga ccc gag gca cgc aaa tgg      2352
Glu Leu Gln Ala Leu Ile Arg Lys Leu Gly Pro Glu Ala Arg Lys Trp
770                 775                 780 atc gat ggg gtg acc tgc aca ggt ggc tcc aac gtc ggt agc gaa ctg      2400
Ile Asp Gly Val Thr Cys Thr Gly Gly Ser Asn Val Gly Ser Glu Leu
785             790                 795                 800 gag ccc ata ctg aac gat gac att gtt agg ctc tca gct cca ccg gtg      2448
Glu Pro Ile Leu Asn Asp Asp Ile Val Arg Leu Ser Ala Pro Pro Val
                805                 810                 815 cgt cga gag atg ccc agc acc aca gtt acc gag atg acg tcc gtg gat      2496
Arg Arg Glu Met Pro Ser Thr Thr Val Thr Glu Met Thr Ser Val Asp
            820                 825                 830 agt gtg acc tcg act cat gtg gag atg gat aac tcc ttt gtg tcg gtg      2544
Ser Val Thr Ser Thr His Val Glu Met Asp Asn Ser Phe Val Ser Val
        835                 840                 845 cag tct aca gtg atg gcg cca tcg ctt cct ccc aaa aag aaa aag caa      2592
Gln Ser Thr Val Met Ala Pro Ser Leu Pro Pro Lys Lys Lys Lys Gln
850                 855                 860 tcg att gta gag cac cac tcg cat gcc cct gct cca act atg atg cag      2640
Ser Ile Val Glu His His Ser His Ala Pro Ala Pro Thr Met Met Gln
865             870                 875                 880 ccc atc cag cag caa ctg cag cag cac tta cag caa cat cag cag atg      2688
Pro Ile Gln Gln Gln Leu Gln Gln His Leu Gln Gln His Gln Gln Met
                885                 890                 895 cag cag cag cac ctg cag cag cag caa cac cag cag atg caa cag caa      2736
Gln Gln Gln His Leu Gln Gln Gln Gln His Gln Gln Met Gln Gln Gln
            900                 905                 910 cag cag cag cag cag cat cat cat cgc cat ctg gag aag aga aac tcg      2784
Gln Gln Gln Gln Gln His His His Arg His Leu Glu Lys Arg Asn Ser
        915                 920                 925 gtg tcc gct cag acc gat gat aat ata ggc agc atc acc agt acg gcg      2832
Val Ser Ala Gln Thr Asp Asp Asn Ile Gly Ser Ile Thr Ser Thr Ala
930                 935                 940 ggc aag cgg agc gga gga gac tgc tcc agc atg cgg gag agg cgt caa      2880
Gly Lys Arg Ser Gly Gly Asp Cys Ser Ser Met Arg Glu Arg Arg Gln
945                 950                 955                 960 tcg acc gcc tcc agg cac tac gac agt ggc agc cag acg ccc acc gcc      2928
Ser Thr Ala Ser Arg His Tyr Asp Ser Gly Ser Gln Thr Pro Thr Ala
                965                 970                 975 cgg cca aag tac agc agc tcg cac cgg aac tcc tcc acc aac atc tcc      2976
Arg Pro Lys Tyr Ser Ser Ser His Arg Asn Ser Ser Thr Asn Ile Ser
            980                 985                 990 aca tcg caa tcg gag ttg agc aac atg tgt cca cac tca aag ccc agt      3024
Thr Ser Gln Ser Glu Leu Ser Asn Met Cys Pro His Ser Lys Pro Ser
        995                 1000                1005
```

-continued

```
act ccg gct gtg att aag act ccc act gcc tcc gac cat cgc cgc acc      3072
Thr Pro Ala Val Ile Lys Thr Pro Thr Ala Ser Asp His Arg Arg Thr
   1010                1015                1020 agc atg ggc tcc gct ctg aag tcc aat ttc gtg gtt tca cag agt gac      3120
Ser Met Gly Ser Ala Leu Lys Ser Asn Phe Val Val Ser Gln Ser Asp
1025                1030                1035                1040 ctc tgg gac acg cac acg ctg tcg cac gcc aag cag cgc cag tcg ccg      3168
Leu Trp Asp Thr His Thr Leu Ser His Ala Lys Gln Arg Gln Ser Pro
            1045                1050                1055 cgg aac tac gcc agt ccg cag cgc tgt gcg gaa cat cat ggc ggc cac      3216
Arg Asn Tyr Ala Ser Pro Gln Arg Cys Ala Glu His His Gly Gly His
        1060                1065                1070 ggg atg acc tat gac ccg aac acc acc tcg ccc atc cag cgg tcc gtc      3264
Gly Met Thr Tyr Asp Pro Asn Thr Thr Ser Pro Ile Gln Arg Ser Val
    1075                1080                1085 tcc gag aag aac cgc aac aaa cat cgg cca aaa ccg caa aag ggc acc      3312
Ser Glu Lys Asn Arg Asn Lys His Arg Pro Lys Pro Gln Lys Gly Thr
1090                1095                1100 gtt tgc cag agc gag acg gac agc gaa cgg gaa cga gat ccg ccg ccc      3360
Val Cys Gln Ser Glu Thr Asp Ser Glu Arg Glu Arg Asp Pro Pro Pro
1105                1110                1115                1120 aac agt cag ccg tgc gtc cag ccg cgt aag gtc agc cgg agc tct aac      3408
Asn Ser Gln Pro Cys Val Gln Pro Arg Lys Val Ser Arg Ser Ser Asn
            1125                1130                1135 atc cag cac gcc gcc cac cac cac agt tcg ccc aat gtg gcg ccc gat      3456
Ile Gln His Ala Ala His His His Ser Ser Pro Asn Val Ala Pro Asp
        1140                1145                1150 aag cag cgg agc agg cag cgc ggc aag cag gat agc agc atc tac ggc      3504
Lys Gln Arg Ser Arg Gln Arg Gly Lys Gln Asp Ser Ser Ile Tyr Gly
    1155                1160                1165 gcc agc agc gag acg gaa ctg ctc gag ggc gag acg gca att ttg ccc      3552
Ala Ser Ser Glu Thr Glu Leu Leu Glu Gly Glu Thr Ala Ile Leu Pro
1170                1175                1180 atc ttc cgg aaa ctc ctc acc gag aag agt ccc aac tat cgg ggc cgc      3600
Ile Phe Arg Lys Leu Leu Thr Glu Lys Ser Pro Asn Tyr Arg Gly Arg
1185                1190                1195                1200 agt gcc gtg ggc cag agc tgt ccg aat ata tcc atc aaa tgc gat atc      3648
Ser Ala Val Gly Gln Ser Cys Pro Asn Ile Ser Ile Lys Cys Asp Ile
            1205                1210                1215 gtc gag tac ttg tag                                                  3663
Val Glu Tyr Leu
        1220
```

<210> SEQ ID NO 4
<211> LENGTH: 1220
<212> TYPE: PRT
<213> ORGANISM: Drosophila melanogaster

<400> SEQUENCE: 4

```
Met Phe Arg Pro Ser Trp Phe Pro Phe Ala Ser Leu Leu Phe Leu Leu
  1               5                  10                  15

Leu Trp Ser Thr Ala Cys Gly Arg Thr Ala Lys Arg Ser Asp Val Tyr
             20                  25                  30

Ile Ala Gly Phe Phe Pro Tyr Gly Asp Gly Val Glu Asn Ser Tyr Thr
         35                  40                  45

Gly Arg Gly Val Met Pro Ser Val Lys Leu Ala Leu Gly His Val Asn
    50                  55                  60

Glu His Gly Lys Ile Leu Ala Asn Tyr Arg Leu His Met Trp Trp Asn
65                  70                  75                  80
```

```
Asp Thr Gln Cys Asn Ala Ala Val Gly Val Lys Ser Phe Phe Asp Met
                85                  90                  95

Met His Ser Gly Pro Asn Lys Val Met Leu Phe Gly Ala Ala Cys Thr
            100                 105                 110

His Val Thr Asp Pro Ile Ala Lys Ala Ser Lys His Trp His Leu Thr
        115                 120                 125

Gln Leu Ser Tyr Ala Asp Thr His Pro Met Phe Thr Lys Asp Ala Phe
    130                 135                 140

Pro Asn Phe Phe Arg Val Val Pro Ser Glu Asn Ala Phe Asn Ala Pro
145                 150                 155                 160

Arg Leu Ala Leu Leu Lys Glu Phe Asn Trp Thr Arg Val Gly Thr Val
                165                 170                 175

Tyr Gln Asn Glu Pro Arg Tyr Ser Leu Pro His Asn His Met Val Ala
            180                 185                 190

Asp Leu Asp Ala Met Glu Val Glu Val Val Glu Thr Gln Ser Phe Val
        195                 200                 205

Asn Asp Val Ala Glu Ser Leu Lys Lys Leu Arg Glu Lys Asp Val Arg
    210                 215                 220

Ile Ile Leu Gly Asn Phe Asn Glu His Phe Ala Arg Lys Ala Phe Cys
225                 230                 235                 240

Glu Ala Tyr Lys Leu Asp Met Tyr Gly Arg Ala Tyr Gln Trp Leu Ile
                245                 250                 255

Met Ala Thr Tyr Ser Thr Asp Trp Trp Asn Val Thr Gln Asp Ser Glu
            260                 265                 270

Cys Ser Val Glu Glu Ile Ala Thr Ala Leu Glu Gly Ala Ile Leu Val
        275                 280                 285

Asp Leu Leu Pro Leu Ser Thr Ser Gly Asp Ile Thr Val Ala Gly Ile
    290                 295                 300

Thr Ala Asp Glu Tyr Leu Val Glu Tyr Asp Arg Leu Arg Gly Thr Glu
305                 310                 315                 320

Tyr Ser Arg Phe His Gly Tyr Thr Tyr Asp Gly Ile Trp Ala Ala Ala
                325                 330                 335

Leu Ala Ile Gln Tyr Val Ala Glu Lys Arg Glu Asp Leu Leu Thr His
            340                 345                 350

Phe Asp Tyr Arg Val Lys Asp Trp Glu Ser Val Phe Leu Glu Ala Leu
        355                 360                 365

Arg Asn Thr Ser Phe Glu Gly Val Thr Gly Pro Val Arg Phe Tyr Asn
    370                 375                 380

Asn Glu Arg Lys Ala Asn Ile Leu Ile Asn Gln Phe Gln Leu Gly Gln
385                 390                 395                 400

Met Glu Lys Ile Gly Glu Tyr His Ser Gln Lys Ser His Leu Asp Leu
                405                 410                 415

Ser Leu Gly Lys Pro Val Lys Trp Val Gly Lys Thr Pro Pro Lys Asp
            420                 425                 430

Arg Thr Leu Ile Tyr Ile Glu His Ser Gln Val Asn Pro Thr Ile Tyr
        435                 440                 445

Ile Val Ser Ala Ser Ala Ser Val Ile Gly Val Ile Ala Thr Val
    450                 455                 460

Phe Leu Ala Phe Asn Ile Lys Tyr Arg Asn Gln Arg Tyr Ile Lys Met
465                 470                 475                 480

Ser Ser Pro His Leu Asn Asn Leu Ile Ile Val Gly Cys Met Ile Thr
                485                 490                 495
```

-continued

```
Tyr Leu Ser Ile Ile Phe Leu Gly Leu Asp Thr Thr Leu Ser Ser Val
                500                 505                 510

Ala Ala Phe Pro Tyr Ile Cys Thr Ala Arg Ala Trp Ile Leu Met Ala
                515                 520                 525

Gly Phe Ser Leu Ser Phe Gly Ala Met Phe Ser Lys Thr Trp Arg Val
                530                 535                 540

His Ser Ile Phe Thr Asp Leu Lys Leu Asn Lys Lys Val Ile Lys Asp
545                 550                 555                 560

Tyr Gln Leu Phe Met Val Val Gly Val Leu Leu Ala Ile Asp Ile Ala
                565                 570                 575

Ile Ile Thr Thr Trp Gln Ile Ala Asp Pro Phe Tyr Arg Glu Thr Lys
                580                 585                 590

Gln Leu Glu Pro Leu His His Glu Asn Ile Asp Asp Val Leu Val Ile
                595                 600                 605

Pro Glu Asn Glu Tyr Cys Gln Ser Glu His Met Thr Ile Phe Val Ser
                610                 615                 620

Ile Ile Tyr Ala Tyr Lys Gly Leu Leu Leu Val Phe Gly Ala Phe Leu
625                 630                 635                 640

Ala Trp Glu Thr Arg His Val Ser Ile Pro Ala Leu Asn Asp Ser Lys
                645                 650                 655

His Ile Gly Phe Ser Val Tyr Asn Val Phe Ile Thr Cys Leu Ala Gly
                660                 665                 670

Ala Ala Ile Ser Leu Val Leu Ser Asp Arg Lys Asp Leu Val Phe Val
                675                 680                 685

Leu Leu Ser Phe Phe Ile Ile Phe Cys Thr Thr Ala Thr Leu Cys Leu
                690                 695                 700

Val Phe Val Pro Lys Leu Val Glu Leu Lys Arg Asn Pro Gln Gly Val
705                 710                 715                 720

Val Asp Lys Arg Val Arg Ala Thr Leu Arg Pro Met Ser Lys Asn Gly
                725                 730                 735

Arg Arg Asp Ser Ser Val Cys Glu Leu Glu Gln Arg Leu Arg Asp Val
                740                 745                 750

Lys Asn Thr Asn Cys Arg Phe Arg Lys Ala Leu Met Glu Lys Glu Asn
                755                 760                 765

Glu Leu Gln Ala Leu Ile Arg Lys Leu Gly Pro Glu Ala Arg Lys Trp
                770                 775                 780

Ile Asp Gly Val Thr Cys Thr Gly Gly Ser Asn Val Gly Ser Glu Leu
785                 790                 795                 800

Glu Pro Ile Leu Asn Asp Asp Ile Val Arg Leu Ser Ala Pro Pro Val
                805                 810                 815

Arg Arg Glu Met Pro Ser Thr Thr Val Thr Glu Met Thr Ser Val Asp
                820                 825                 830

Ser Val Thr Ser Thr His Val Glu Met Asp Asn Ser Phe Val Ser Val
                835                 840                 845

Gln Ser Thr Val Met Ala Pro Ser Leu Pro Pro Lys Lys Lys Lys Gln
                850                 855                 860

Ser Ile Val Glu His His His Ser His Ala Pro Ala Pro Thr Met Met Gln
865                 870                 875                 880

Pro Ile Gln Gln Gln Leu Gln Gln His Leu Gln Gln His Gln Gln Met
                885                 890                 895

Gln Gln Gln His Leu Gln Gln Gln His Gln Gln Met Gln Gln Gln
                900                 905                 910

Gln Gln Gln Gln Gln His His His Arg His Leu Glu Lys Arg Asn Ser
```

```
                915                 920                 925
Val Ser Ala Gln Thr Asp Asp Asn Ile Gly Ser Ile Thr Ser Thr Ala
    930                 935                 940

Gly Lys Arg Ser Gly Gly Asp Cys Ser Ser Met Arg Glu Arg Arg Gln
945                 950                 955                 960

Ser Thr Ala Ser Arg His Tyr Asp Ser Gly Ser Gln Thr Pro Thr Ala
                965                 970                 975

Arg Pro Lys Tyr Ser Ser Ser His Arg Asn Ser Ser Thr Asn Ile Ser
                    980                 985                 990

Thr Ser Gln Ser Glu Leu Ser Asn Met Cys Pro His Ser Lys Pro Ser
            995                 1000                1005

Thr Pro Ala Val Ile Lys Thr Pro Thr Ala Ser Asp His Arg Arg Thr
    1010                1015                1020

Ser Met Gly Ser Ala Leu Lys Ser Asn Phe Val Val Ser Gln Ser Asp
1025                1030                1035                1040

Leu Trp Asp Thr His Thr Leu Ser His Ala Lys Gln Arg Gln Ser Pro
                1045                1050                1055

Arg Asn Tyr Ala Ser Pro Gln Arg Cys Ala Glu His His Gly Gly His
                    1060                1065                1070

Gly Met Thr Tyr Asp Pro Asn Thr Thr Ser Pro Ile Gln Arg Ser Val
            1075                1080                1085

Ser Glu Lys Asn Arg Asn Lys His Arg Pro Lys Pro Gln Lys Gly Thr
    1090                1095                1100

Val Cys Gln Ser Glu Thr Asp Ser Glu Arg Glu Arg Asp Pro Pro Pro
1105                1110                1115                1120

Asn Ser Gln Pro Cys Val Gln Pro Arg Lys Val Ser Arg Ser Ser Asn
                1125                1130                1135

Ile Gln His Ala Ala His His His Ser Ser Pro Asn Val Ala Pro Asp
                    1140                1145                1150

Lys Gln Arg Ser Arg Gln Arg Gly Lys Gln Asp Ser Ser Ile Tyr Gly
            1155                1160                1165

Ala Ser Ser Glu Thr Glu Leu Leu Glu Gly Glu Thr Ala Ile Leu Pro
    1170                1175                1180

Ile Phe Arg Lys Leu Leu Thr Glu Lys Ser Pro Asn Tyr Arg Gly Arg
1185                1190                1195                1200

Ser Ala Val Gly Gln Ser Cys Pro Asn Ile Ser Ile Lys Cys Asp Ile
                1205                1210                1215

Val Glu Tyr Leu
        1220

<210> SEQ ID NO 5
<211> LENGTH: 3918
<212> TYPE: DNA
<213> ORGANISM: Drosophila melanogaster
<220> FEATURE:
<221> NAME/KEY: CDS
<222> LOCATION: (1)..(3915)

<400> SEQUENCE: 5 atg cgc ata att caa ccg gtc caa ggg acc aga tac ggt cca tgg ccg    48
Met Arg Ile Ile Gln Pro Val Gln Gly Thr Arg Tyr Gly Pro Trp Pro
  1               5                  10                  15 gcc gtg gga ctg agg cta gtc ctg gcc ctt gcc tgg gca acg tcg gca    96
Ala Val Gly Leu Arg Leu Val Leu Ala Leu Ala Trp Ala Thr Ser Ala
             20                  25                  30 gcg gct gcc atg gag tca tca gcc gag ctg cag gcc ctg ggc cac gag   144
Ala Ala Ala Met Glu Ser Ser Ala Glu Leu Gln Ala Leu Gly His Glu
```

```
                                                        -continued

Ala Ala Ala Met Glu Ser Ser Ala Glu Leu Gln Ala Leu Gly His Glu
         35                  40                  45 gca att agg cca ggt gct gcc tca att agc aca tcc agc cca tcc agc        192
Ala Ile Arg Pro Gly Ala Ala Ser Ile Ser Thr Ser Ser Pro Ser Ser
 50                  55                  60 tcg cca ccc gga gaa tcg gca tcg act gtg act gca ggg ggg act ccg        240
Ser Pro Pro Gly Glu Ser Ala Ser Thr Val Thr Ala Gly Gly Thr Pro
 65                  70                  75                  80 att cca ccg cgc tcc gat tgg aag tac aaa cgg acg aaa gtc aaa cgc        288
Ile Pro Pro Arg Ser Asp Trp Lys Tyr Lys Arg Thr Lys Val Lys Arg
                 85                  90                  95 cgg cag cag cgc ctc aat tcg cac agc aat ctg ccc gga agc acc aat        336
Arg Gln Gln Arg Leu Asn Ser His Ser Asn Leu Pro Gly Ser Thr Asn
            100                 105                 110 gcc tcc cac gct cac cac ctc ctc aat ctg ccc ccc agg cag cga tac        384
Ala Ser His Ala His His Leu Leu Asn Leu Pro Pro Arg Gln Arg Tyr
        115                 120                 125 ttg aag gtc aac cag gtg ttc gaa agc gaa cgc gcc atg tcg ccg gcc        432
Leu Lys Val Asn Gln Val Phe Glu Ser Glu Arg Ala Met Ser Pro Ala
    130                 135                 140 gaa atg cag cgc aat cat ggc aaa atc gtg ctg ctc gga ctc ttt gag        480
Glu Met Gln Arg Asn His Gly Lys Ile Val Leu Leu Gly Leu Phe Glu
145                 150                 155                 160 ctg tcc aca tcg cgg gga cca cgt ccg gat ggt ctg agc gaa ttg gga        528
Leu Ser Thr Ser Arg Gly Pro Arg Pro Asp Gly Leu Ser Glu Leu Gly
                165                 170                 175 gct gcc acc atg gcc gtg gaa cac atc aac cgc aag cgc ctg ctg ccg        576
Ala Ala Thr Met Ala Val Glu His Ile Asn Arg Lys Arg Leu Leu Pro
            180                 185                 190 ggc tac acc ctc gag ctc gtg acc aac gat act cag tgt gat cct gga        624
Gly Tyr Thr Leu Glu Leu Val Thr Asn Asp Thr Gln Cys Asp Pro Gly
        195                 200                 205 gtg ggc gtg gat cgc ttc ttc cac gcc atc tac aca cag ccc tcg acg        672
Val Gly Val Asp Arg Phe Phe His Ala Ile Tyr Thr Gln Pro Ser Thr
    210                 215                 220 agg atg gtg atg ctg ctg gga tcg gcc tgc tcg gag gtc acc gag agc        720
Arg Met Val Met Leu Leu Gly Ser Ala Cys Ser Glu Val Thr Glu Ser
225                 230                 235                 240 ctg gcg aag gtg gtg ccc tac tgg aac atc gtg cag gta tcc ttc ggt        768
Leu Ala Lys Val Val Pro Tyr Trp Asn Ile Val Gln Val Ser Phe Gly
                245                 250                 255 tcc aca tcg ccg gcg ttg agc gac agg cgg gag ttc ccc tac ttc tac        816
Ser Thr Ser Pro Ala Leu Ser Asp Arg Arg Glu Phe Pro Tyr Phe Tyr
            260                 265                 270 agg aca gtg gcc ccg gac tcc tca cac aat ccg gcg cgc atc gct ttc        864
Arg Thr Val Ala Pro Asp Ser Ser His Asn Pro Ala Arg Ile Ala Phe
        275                 280                 285 att cgg aag ttt ggc tgg ggc acg gtg acc act ttc tcg cag aac gag        912
Ile Arg Lys Phe Gly Trp Gly Thr Val Thr Thr Phe Ser Gln Asn Glu
    290                 295                 300 gag gtt cac tcg ctg gcg gtg aac aac ctg gtc acc gaa ctg gag gcg        960
Glu Val His Ser Leu Ala Val Asn Asn Leu Val Thr Glu Leu Glu Ala
305                 310                 315                 320 gcc aac ata tcc tgt gcc gcc acc atc acc ttt gcg gcc acc gac ttc       1008
Ala Asn Ile Ser Cys Ala Ala Thr Ile Thr Phe Ala Ala Thr Asp Phe
                325                 330                 335 aag gag cag ctg ctg cta ctt agg gag acg gac acg cgc atc atc atc       1056
Lys Glu Gln Leu Leu Leu Leu Arg Glu Thr Asp Thr Arg Ile Ile Ile
            340                 345                 350
```

```
ggc agc ttc tcg cag gag ctg gcc ccc cag atc ctg tgc gag gcc tac    1104
Gly Ser Phe Ser Gln Glu Leu Ala Pro Gln Ile Leu Cys Glu Ala Tyr
        355                 360                 365 agg ctt cga atg ttc ggg gcg gac tac gcc tgg atc ctc cac gag agc    1152
Arg Leu Arg Met Phe Gly Ala Asp Tyr Ala Trp Ile Leu His Glu Ser
370                 375                 380 atg ggg gct ccg tgg tgg ccg gac cag cgc acc gcc tgc tct aac cac    1200
Met Gly Ala Pro Trp Trp Pro Asp Gln Arg Thr Ala Cys Ser Asn His
385                 390                 395                 400 gaa ctg cag ctg gcc gtc gag aac ctc atc gtg gtc tca acg cac aac    1248
Glu Leu Gln Leu Ala Val Glu Asn Leu Ile Val Val Ser Thr His Asn
                405                 410                 415 agc atc gtt gga aat aac gtc agc tat agt gga ctg aac aat cac atg    1296
Ser Ile Val Gly Asn Asn Val Ser Tyr Ser Gly Leu Asn Asn His Met
            420                 425                 430 ttc aac tcc cag ctg cgc aag caa tcc gcc cag ttc cac ggc cag gat    1344
Phe Asn Ser Gln Leu Arg Lys Gln Ser Ala Gln Phe His Gly Gln Asp
        435                 440                 445 gga ttt ggc tcc ggt tat ggt ccc agg atc agt atc gct gca acg caa    1392
Gly Phe Gly Ser Gly Tyr Gly Pro Arg Ile Ser Ile Ala Ala Thr Gln
450                 455                 460 tct gac tct cgt cgg cgg agg aga agg ggc gtg gta ggc acc agc gga    1440
Ser Asp Ser Arg Arg Arg Arg Arg Gly Val Val Gly Thr Ser Gly
465                 470                 475                 480 ggg cac ctc ttt ccg gag gcg atc tcg cag tac gcg ccg caa acc tac    1488
Gly His Leu Phe Pro Glu Ala Ile Ser Gln Tyr Ala Pro Gln Thr Tyr
                485                 490                 495 gac gcc gtg tgg gcc atc gcc ctg gcc ttg aga gcc gct gag gag cac    1536
Asp Ala Val Trp Ala Ile Ala Leu Ala Leu Arg Ala Ala Glu Glu His
            500                 505                 510 tgg cgg cgg aac gag gag cag tcg aag ctg gac gga ttc gat tac acc    1584
Trp Arg Arg Asn Glu Glu Gln Ser Lys Leu Asp Gly Phe Asp Tyr Thr
        515                 520                 525 cgc agc gac atg gcc tgg gag ttc ctg cag caa atg ggc aag ctc cac    1632
Arg Ser Asp Met Ala Trp Glu Phe Leu Gln Gln Met Gly Lys Leu His
530                 535                 540 ttc ctg gga gtg tcg ggc ccc gtt tcc ttc agc ggc cca gat cgc gtt    1680
Phe Leu Gly Val Ser Gly Pro Val Ser Phe Ser Gly Pro Asp Arg Val
545                 550                 555                 560 ggc acc act gcc ttc tat caa atc cag cgc ggt ttg ctg gaa ccg gtg    1728
Gly Thr Thr Ala Phe Tyr Gln Ile Gln Arg Gly Leu Leu Glu Pro Val
                565                 570                 575 gcc ctc tac tat ccg gcc acg gat gcc ctg gac ttc cgg tgt ccc cgc    1776
Ala Leu Tyr Tyr Pro Ala Thr Asp Ala Leu Asp Phe Arg Cys Pro Arg
            580                 585                 590 tgc cgg ccg gtg aag tgg cac agc ggg cag gta ccc atc gcc aag cgg    1824
Cys Arg Pro Val Lys Trp His Ser Gly Gln Val Pro Ile Ala Lys Arg
        595                 600                 605 gtg ttc aag ctg cgg gtg gcg acc atc gct cca ctg gcc ttc tac acc    1872
Val Phe Lys Leu Arg Val Ala Thr Ile Ala Pro Leu Ala Phe Tyr Thr
610                 615                 620 atc gcc acc ctc tcc agc gtg gga atc gct ctg gcc atc acc ttc ctg    1920
Ile Ala Thr Leu Ser Ser Val Gly Ile Ala Leu Ala Ile Thr Phe Leu
                625                 630                 635                 640 gcg ttc aat ctg cac ttt cgg aag ctg aag gca att aaa ctt tcc agc    1968
Ala Phe Asn Leu His Phe Arg Lys Leu Lys Ala Ile Lys Leu Ser Ser
                    645                 650                 655 ccg aag ctg agc aac atc acc gca gtg ggc tgc atc ttt gtg tac gcc    2016
Pro Lys Leu Ser Asn Ile Thr Ala Val Gly Cys Ile Phe Val Tyr Ala
                660                 665                 670
```

-continued

| | | |
|---|---|---|
| acc gtc atc ctt ttg ggc ttg gac cac tcg acg ctg ccc tcg gcg gag<br>Thr Val Ile Leu Leu Gly Leu Asp His Ser Thr Leu Pro Ser Ala Glu<br>675                        680                          685 | 2064 |
| gac tct ttc gca acg gtc tgc acg gcc cgc gtc tat ctg ctc tcc gcc<br>Asp Ser Phe Ala Thr Val Cys Thr Ala Arg Val Tyr Leu Leu Ser Ala<br>690                        695                          700 | 2112 |
| gga ttc tcg ttg gcc ttt gga tcg atg ttt gcc aag acc tac aga gtg<br>Gly Phe Ser Leu Ala Phe Gly Ser Met Phe Ala Lys Thr Tyr Arg Val<br>705                        710                        715                          720 | 2160 |
| cat cgg ata ttc act cgt acc ggc agc gtt ttc aag gac aag atg ctg<br>His Arg Ile Phe Thr Arg Thr Gly Ser Val Phe Lys Asp Lys Met Leu<br>                    725                        730                        735 | 2208 |
| cag gac att caa ctg atc ttg ctc gtc ggc gga ttg ctt ctg gtg gat<br>Gln Asp Ile Gln Leu Ile Leu Leu Val Gly Gly Leu Leu Leu Val Asp<br>740                        745                          750 | 2256 |
| gcg ctg ctc gta acc ctt tgg gtg gtc acc gat cca atg gag cgc cat<br>Ala Leu Leu Val Thr Leu Trp Val Val Thr Asp Pro Met Glu Arg His<br>                    755                        760                        765 | 2304 |
| ctt cac aac ctg acg ctc gag atc agt gcg act gat aga agt gtc gtt<br>Leu His Asn Leu Thr Leu Glu Ile Ser Ala Thr Asp Arg Ser Val Val<br>770                        775                          780 | 2352 |
| tac cag cct cag gtt gaa gtt tgc cgt tcg cag cac acg caa acg tgg<br>Tyr Gln Pro Gln Val Glu Val Cys Arg Ser Gln His Thr Gln Thr Trp<br>785                        790                        795                        800 | 2400 |
| ttg agt gtc ctg tac gcc tac aaa ggc ctt ctt ctt gtg gtg ggt gtc<br>Leu Ser Val Leu Tyr Ala Tyr Lys Gly Leu Leu Leu Val Val Gly Val<br>                    805                        810                        815 | 2448 |
| tat atg gcc tgg gag acg cgc cac gta aaa ata cct gct ctc aat gac<br>Tyr Met Ala Trp Glu Thr Arg His Val Lys Ile Pro Ala Leu Asn Asp<br>820                        825                        830 | 2496 |
| tcg cag tac atc gga gtg tct gta tac agt gtg gtc atc acc agc gcc<br>Ser Gln Tyr Ile Gly Val Ser Val Tyr Ser Val Val Ile Thr Ser Ala<br>                    835                        840                        845 | 2544 |
| atc gtc gtg gtg ctg gcc aac ttg att tcg gag cga gtc acc ctg gcc<br>Ile Val Val Val Leu Ala Asn Leu Ile Ser Glu Arg Val Thr Leu Ala<br>850                        855                        860 | 2592 |
| ttc atc aca atc aca gct ctg att tta acc agc acc act gca acc ctt<br>Phe Ile Thr Ile Thr Ala Leu Ile Leu Thr Ser Thr Thr Ala Thr Leu<br>865                        870                        875                        880 | 2640 |
| tgt ctg ctt ttc atc cca aaa ctc cat gat att tgg gca aga aac gat<br>Cys Leu Leu Phe Ile Pro Lys Leu His Asp Ile Trp Ala Arg Asn Asp<br>                    885                        890                        895 | 2688 |
| att atc gat ccg gtt atc cac agt atg ggc ctt aag atg gag tgc aac<br>Ile Ile Asp Pro Val Ile His Ser Met Gly Leu Lys Met Glu Cys Asn<br>                    900                        905                        910 | 2736 |
| aca cgc cga ttc gtg gtc gat gat cgc cga gaa ctg cag tat cga gtg<br>Thr Arg Arg Phe Val Val Asp Asp Arg Arg Glu Leu Gln Tyr Arg Val<br>                    915                        920                        925 | 2784 |
| gag gtg caa aac agg gtc tat aag aag gaa atc cag gct ctg gac gcc<br>Glu Val Gln Asn Arg Val Tyr Lys Lys Glu Ile Gln Ala Leu Asp Ala<br>930                        935                          940 | 2832 |
| gag att cga aag ctg gag agg cta ctc gag tcg gga cta acc acc acc<br>Glu Ile Arg Lys Leu Glu Arg Leu Leu Glu Ser Gly Leu Thr Thr Thr<br>945                        950                        955                        960 | 2880 |
| tcc acc aca act tcg tcg tcc aca tca ctc tta act ggg gga ggt cat<br>Ser Thr Thr Thr Ser Ser Ser Thr Ser Leu Leu Thr Gly Gly Gly His<br>                    965                        970                        975 | 2928 |
| cta aag cca gaa ctg acg gta acc agt ggc atc tcg cag act ccg gct<br>Leu Lys Pro Glu Leu Thr Val Thr Ser Gly Ile Ser Gln Thr Pro Ala | 2976 |

-continued

| | |
|---|---|
| gca agt aaa aac aga act cca agt atc tcg gga ata ctg ccc aat ctc<br>Ala Ser Lys Asn Arg Thr Pro Ser Ile Ser Gly Ile Leu Pro Asn Leu<br>      995                       1000                      1005 | 3024 |
| ctg ctt tcc gtg ctg cct cct gtg att cca cgg gcc agt tgg ccg tca<br>Leu Leu Ser Val Leu Pro Pro Val Ile Pro Arg Ala Ser Trp Pro Ser<br>   1010                       1015                      1020 | 3072 |
| gca gag tac atg cag atc ccg atg agg cgt tct gtt acc ttt gcc tcc<br>Ala Glu Tyr Met Gln Ile Pro Met Arg Arg Ser Val Thr Phe Ala Ser<br>1025                    1030                    1035                 1040 | 3120 |
| cag ccc caa tta gag gag gcc tgc ctg cct gca cag gac ttg att aac<br>Gln Pro Gln Leu Glu Glu Ala Cys Leu Pro Ala Gln Asp Leu Ile Asn<br>                   1045                    1050                 1055 | 3168 |
| ctc cgt tta gcc cac cag cag gcc acg gag gct aag acg ggc ttg ata<br>Leu Arg Leu Ala His Gln Gln Ala Thr Glu Ala Lys Thr Gly Leu Ile<br>          1060                      1065                    1070 | 3216 |
| aac cga tta cga ggg ata ttt tct cgc acc act tcg agc aac aag gga<br>Asn Arg Leu Arg Gly Ile Phe Ser Arg Thr Thr Ser Ser Asn Lys Gly<br>       1075                     1080                    1085 | 3264 |
| tcc acc gcc agc ttg gcg gac caa aag ggt ctg aag gcg gcc ttt aaa<br>Ser Thr Ala Ser Leu Ala Asp Gln Lys Gly Leu Lys Ala Ala Phe Lys<br>   1090                       1095                      1100 | 3312 |
| tcg cac atg gga ctg ttc acc cgc ctg att ccc tcc tct caa acg gcg<br>Ser His Met Gly Leu Phe Thr Arg Leu Ile Pro Ser Ser Gln Thr Ala<br>1105                    1110                    1115                 1120 | 3360 |
| tcc tgc aat gcc ata tac aat aat cca aat cag gat tcc att ccc tca<br>Ser Cys Asn Ala Ile Tyr Asn Asn Pro Asn Gln Asp Ser Ile Pro Ser<br>             1125                    1130                 1135 | 3408 |
| gag gcg tcc tcc cac ccg aat ggt aac cac cta aag ccc atc cat agg<br>Glu Ala Ser Ser His Pro Asn Gly Asn His Leu Lys Pro Ile His Arg<br>          1140                      1145                    1150 | 3456 |
| ggt tca ttg acc aaa agc ggt act cac ctg gat cac ctt acc aag gat<br>Gly Ser Leu Thr Lys Ser Gly Thr His Leu Asp His Leu Thr Lys Asp<br>       1155                     1160                    1165 | 3504 |
| ccg aat ttc ctg cct atc ccc act att tct ggc ggt gaa cag ggg gac<br>Pro Asn Phe Leu Pro Ile Pro Thr Ile Ser Gly Gly Glu Gln Gly Asp<br>   1170                       1175                    1180 | 3552 |
| caa acg ttg ggt gga aag tat gtg aaa ctg ctg gag acc aag gtg aac<br>Gln Thr Leu Gly Gly Lys Tyr Val Lys Leu Leu Glu Thr Lys Val Asn<br>1185                    1190                    1195                 1200 | 3600 |
| ttc caa ttg ccc agc aac cgg aga cct tcg gtg gtg cag cag cca ccc<br>Phe Gln Leu Pro Ser Asn Arg Arg Pro Ser Val Val Gln Gln Pro Pro<br>                   1205                    1210                 1215 | 3648 |
| agt tta agg gaa agg gta agg ggt tcg cca cgc ttt cca cac cgc atc<br>Ser Leu Arg Glu Arg Val Arg Gly Ser Pro Arg Phe Pro His Arg Ile<br>          1220                      1225                    1230 | 3696 |
| ctg ccg ccc act tgc agt ctc agc gcc ctg gcc gaa tcc gag gac cgt<br>Leu Pro Pro Thr Cys Ser Leu Ser Ala Leu Ala Glu Ser Glu Asp Arg<br>       1235                     1240                    1245 | 3744 |
| ccc gga gat agc acc tct atc ttg ggc agc tgc aag tcc ata cct cgc<br>Pro Gly Asp Ser Thr Ser Ile Leu Gly Ser Cys Lys Ser Ile Pro Arg<br>   1250                       1255                    1260 | 3792 |
| att tcg ctg cag cag gtc acc agt gga ggc acc tgg aaa tcg atg gaa<br>Ile Ser Leu Gln Gln Val Thr Ser Gly Gly Thr Trp Lys Ser Met Glu<br>1265                    1270                    1275                 1280 | 3840 |
| aca gtg ggc aag tcg agg ctt tcc ctc ggc gat tcc cag gaa gag gag<br>Thr Val Gly Lys Ser Arg Leu Ser Leu Gly Asp Ser Gln Glu Glu Glu<br>                   1285                    1290                 1295 | 3888 |
| cag cag gcg cct gcg aat ggc acc gaa taa | 3918 |

-continued

```
Gln Gln Ala Pro Ala Asn Gly Thr Glu
        1300                1305

<210> SEQ ID NO 6
<211> LENGTH: 1305
<212> TYPE: PRT
<213> ORGANISM: Drosophila melanogaster

<400> SEQUENCE: 6

Met Arg Ile Ile Gln Pro Val Gln Gly Thr Arg Tyr Gly Pro Trp Pro
 1               5                  10                  15

Ala Val Gly Leu Arg Leu Val Leu Ala Leu Ala Trp Ala Thr Ser Ala
            20                  25                  30

Ala Ala Ala Met Glu Ser Ser Ala Glu Leu Gln Ala Leu Gly His Glu
        35                  40                  45

Ala Ile Arg Pro Gly Ala Ala Ser Ile Ser Thr Ser Ser Pro Ser Ser
    50                  55                  60

Ser Pro Pro Gly Glu Ser Ala Ser Val Thr Ala Gly Gly Thr Pro
 65                 70                  75                  80

Ile Pro Pro Arg Ser Asp Trp Lys Tyr Lys Arg Thr Lys Val Lys Arg
                85                  90                  95

Arg Gln Gln Arg Leu Asn Ser His Ser Asn Leu Pro Gly Ser Thr Asn
            100                 105                 110

Ala Ser His Ala His His Leu Leu Asn Leu Pro Pro Arg Gln Arg Tyr
        115                 120                 125

Leu Lys Val Asn Gln Val Phe Glu Ser Glu Arg Met Ser Pro Ala
    130                 135                 140

Glu Met Gln Arg Asn His Gly Lys Ile Val Leu Leu Gly Leu Phe Glu
145                 150                 155                 160

Leu Ser Thr Ser Arg Gly Pro Arg Pro Asp Gly Leu Ser Glu Leu Gly
                165                 170                 175

Ala Ala Thr Met Ala Val Glu His Ile Asn Arg Lys Arg Leu Leu Pro
            180                 185                 190

Gly Tyr Thr Leu Glu Leu Val Thr Asn Asp Thr Gln Cys Asp Pro Gly
        195                 200                 205

Val Gly Val Asp Arg Phe Phe His Ala Ile Tyr Thr Gln Pro Ser Thr
    210                 215                 220

Arg Met Val Met Leu Leu Gly Ser Ala Cys Ser Glu Val Thr Glu Ser
225                 230                 235                 240

Leu Ala Lys Val Val Pro Tyr Trp Asn Ile Val Gln Val Ser Phe Gly
                245                 250                 255

Ser Thr Ser Pro Ala Leu Ser Asp Arg Arg Glu Phe Pro Tyr Phe Tyr
            260                 265                 270

Arg Thr Val Ala Pro Asp Ser Ser His Asn Pro Ala Arg Ile Ala Phe
        275                 280                 285

Ile Arg Lys Phe Gly Trp Gly Thr Val Thr Thr Phe Ser Gln Asn Glu
    290                 295                 300

Glu Val His Ser Leu Ala Val Asn Asn Leu Val Thr Glu Leu Glu Ala
305                 310                 315                 320

Ala Asn Ile Ser Cys Ala Ala Thr Ile Thr Phe Ala Ala Thr Asp Phe
                325                 330                 335

Lys Glu Gln Leu Leu Leu Arg Glu Thr Asp Thr Arg Ile Ile Ile
            340                 345                 350

Gly Ser Phe Ser Gln Glu Leu Ala Pro Gln Ile Leu Cys Glu Ala Tyr
        355                 360                 365
```

-continued

```
Arg Leu Arg Met Phe Gly Ala Asp Tyr Ala Trp Ile Leu His Glu Ser
    370                 375                 380

Met Gly Ala Pro Trp Trp Pro Asp Gln Arg Thr Ala Cys Ser Asn His
385                 390                 395                 400

Glu Leu Gln Leu Ala Val Glu Asn Leu Ile Val Val Ser Thr His Asn
                405                 410                 415

Ser Ile Val Gly Asn Asn Val Ser Tyr Ser Gly Leu Asn Asn His Met
            420                 425                 430

Phe Asn Ser Gln Leu Arg Lys Gln Ser Ala Gln Phe His Gly Gln Asp
        435                 440                 445

Gly Phe Gly Ser Gly Tyr Gly Pro Arg Ile Ser Ile Ala Ala Thr Gln
    450                 455                 460

Ser Asp Ser Arg Arg Arg Arg Arg Gly Val Val Gly Thr Ser Gly
465                 470                 475                 480

Gly His Leu Phe Pro Glu Ala Ile Ser Gln Tyr Ala Pro Gln Thr Tyr
                485                 490                 495

Asp Ala Val Trp Ala Ile Ala Leu Ala Leu Arg Ala Ala Glu Glu His
            500                 505                 510

Trp Arg Arg Asn Glu Glu Gln Ser Lys Leu Asp Gly Phe Asp Tyr Thr
        515                 520                 525

Arg Ser Asp Met Ala Trp Glu Phe Leu Gln Gln Met Gly Lys Leu His
    530                 535                 540

Phe Leu Gly Val Ser Gly Pro Val Ser Phe Ser Gly Pro Asp Arg Val
545                 550                 555                 560

Gly Thr Thr Ala Phe Tyr Gln Ile Gln Arg Gly Leu Leu Glu Pro Val
                565                 570                 575

Ala Leu Tyr Tyr Pro Ala Thr Asp Ala Leu Asp Phe Arg Cys Pro Arg
            580                 585                 590

Cys Arg Pro Val Lys Trp His Ser Gly Gln Val Pro Ile Ala Lys Arg
        595                 600                 605

Val Phe Lys Leu Arg Val Ala Thr Ile Ala Pro Leu Ala Phe Tyr Thr
    610                 615                 620

Ile Ala Thr Leu Ser Ser Val Gly Ile Ala Leu Ala Ile Thr Phe Leu
625                 630                 635                 640

Ala Phe Asn Leu His Phe Arg Lys Leu Lys Ala Ile Lys Leu Ser Ser
                645                 650                 655

Pro Lys Leu Ser Asn Ile Thr Ala Val Gly Cys Ile Phe Val Tyr Ala
            660                 665                 670

Thr Val Ile Leu Leu Gly Leu Asp His Ser Thr Leu Pro Ser Ala Glu
        675                 680                 685

Asp Ser Phe Ala Thr Val Cys Thr Ala Arg Val Tyr Leu Leu Ser Ala
    690                 695                 700

Gly Phe Ser Leu Ala Phe Gly Ser Met Phe Ala Lys Thr Tyr Arg Val
705                 710                 715                 720

His Arg Ile Phe Thr Arg Thr Gly Ser Val Phe Lys Asp Lys Met Leu
                725                 730                 735

Gln Asp Ile Gln Leu Ile Leu Val Gly Gly Leu Leu Leu Val Asp
            740                 745                 750

Ala Leu Leu Val Thr Leu Trp Val Val Thr Asp Pro Met Glu Arg His
        755                 760                 765

Leu His Asn Leu Thr Leu Glu Ile Ser Ala Thr Asp Arg Ser Val Val
    770                 775                 780
```

-continued

```
Tyr Gln Pro Gln Val Glu Val Cys Arg Ser Gln His Thr Gln Thr Trp
785                 790                 795                 800

Leu Ser Val Leu Tyr Ala Tyr Lys Gly Leu Leu Val Val Gly Val
            805                 810                 815

Tyr Met Ala Trp Glu Thr Arg His Val Lys Ile Pro Ala Leu Asn Asp
            820                 825                 830

Ser Gln Tyr Ile Gly Val Ser Val Tyr Ser Val Val Ile Thr Ser Ala
            835                 840                 845

Ile Val Val Val Leu Ala Asn Leu Ile Ser Glu Arg Val Thr Leu Ala
        850                 855                 860

Phe Ile Thr Ile Thr Ala Leu Ile Leu Thr Ser Thr Ala Thr Leu
865                 870                 875                 880

Cys Leu Leu Phe Ile Pro Lys Leu His Asp Ile Trp Ala Arg Asn Asp
                885                 890                 895

Ile Ile Asp Pro Val Ile His Ser Met Gly Leu Lys Met Glu Cys Asn
                900                 905                 910

Thr Arg Arg Phe Val Val Asp Asp Arg Arg Glu Leu Gln Tyr Arg Val
            915                 920                 925

Glu Val Gln Asn Arg Val Tyr Lys Lys Glu Ile Gln Ala Leu Asp Ala
        930                 935                 940

Glu Ile Arg Lys Leu Glu Arg Leu Leu Glu Ser Gly Leu Thr Thr Thr
945                 950                 955                 960

Ser Thr Thr Thr Ser Ser Ser Thr Ser Leu Leu Thr Gly Gly Gly His
                965                 970                 975

Leu Lys Pro Glu Leu Thr Val Thr Ser Gly Ile Ser Gln Thr Pro Ala
            980                 985                 990

Ala Ser Lys Asn Arg Thr Pro Ser Ile Ser Gly Ile Leu Pro Asn Leu
            995                 1000                1005

Leu Leu Ser Val Leu Pro Pro Val Ile Pro Arg Ala Ser Trp Pro Ser
        1010                1015                1020

Ala Glu Tyr Met Gln Ile Pro Met Arg Arg Ser Val Thr Phe Ala Ser
1025                1030                1035                1040

Gln Pro Gln Leu Glu Glu Ala Cys Leu Pro Ala Gln Asp Leu Ile Asn
                1045                1050                1055

Leu Arg Leu Ala His Gln Gln Ala Thr Glu Ala Lys Thr Gly Leu Ile
                1060                1065                1070

Asn Arg Leu Arg Gly Ile Phe Ser Arg Thr Thr Ser Ser Asn Lys Gly
            1075                1080                1085

Ser Thr Ala Ser Leu Ala Asp Gln Lys Gly Leu Lys Ala Ala Phe Lys
1090                1095                1100

Ser His Met Gly Leu Phe Thr Arg Leu Ile Pro Ser Ser Gln Thr Ala
1105                1110                1115                1120

Ser Cys Asn Ala Ile Tyr Asn Asn Pro Asn Gln Asp Ser Ile Pro Ser
                1125                1130                1135

Glu Ala Ser Ser His Pro Asn Gly Asn His Leu Lys Pro Ile His Arg
                1140                1145                1150

Gly Ser Leu Thr Lys Ser Gly Thr His Leu Asp His Leu Thr Lys Asp
            1155                1160                1165

Pro Asn Phe Leu Pro Ile Pro Thr Ile Ser Gly Gly Glu Gln Gly Asp
            1170                1175                1180

Gln Thr Leu Gly Gly Lys Tyr Val Lys Leu Leu Glu Thr Lys Val Asn
1185                1190                1195                1200

Phe Gln Leu Pro Ser Asn Arg Arg Pro Ser Val Val Gln Gln Pro Pro
```

-continued

```
            1205                1210                  1215
Ser Leu Arg Glu Arg Val Arg Gly Ser Pro Arg Phe Pro His Arg Ile
        1220                1225                1230
Leu Pro Pro Thr Cys Ser Leu Ser Ala Leu Ala Glu Ser Glu Asp Arg
    1235                1240                1245
Pro Gly Asp Ser Thr Ser Ile Leu Gly Ser Cys Lys Ser Ile Pro Arg
1250                1255                1260
Ile Ser Leu Gln Gln Val Thr Ser Gly Gly Thr Trp Lys Ser Met Glu
1265                1270                1275                1280
Thr Val Gly Lys Ser Arg Leu Ser Leu Gly Asp Ser Gln Glu Glu
        1285                1290                1295
Gln Gln Ala Pro Ala Asn Gly Thr Glu
        1300                1305
```

GABA B RECEPTORS

The invention relates to polypeptides which exert the biological activity of GABA B receptors and to nucleic acids encoding these polypeptides, and, in particular, to their use for finding active compounds for crop protection.

BACKGROUND OF THE INVENTION

Gamma-amino-butyric acid (GABA) is the most important inhibitory neuro-transmitter in the nervous system of vertebrates and invertebrates. The GABA receptors can be classified into two subfamilies, the GABA A and GABA B receptors. Amongst these, the GABA A receptors are ligand-controlled ion channels, while the GABA B receptors are metabotropic, G-protein-coupled receptors. GABA B receptors affect the release of various neurotransmitters and the activity of ion channels.

GABA B receptors have been studied extensively, in particular in vertebrates. Two subtypes (GABA B1 and GABA B2), which are functionally active as heterodimers, are known here (Jones et al., 1998; Kaupmann et al., 1998; White et al., 1998).

In insects, GABA is the most important inhibitory neurotransmitter of the central nervous system. Accordingly, GABA receptors can be detected electrophysiologically on preparations of insect central ganglia. Both the GABA A receptors and the GABA B receptors are the molecular target of important natural and synthetic insecticidally active compounds (Sattelle, 1990; Fukunaga et al., 1999).

The protein sequence of a number of insect GABA A receptors is already known. Thus, the sequences of three different subunits have been described for Drosophila melanogaster (ffrench-Constant et al., 1991; Harvey et al., 1994; Henderson et al., 1993).

The provision of insect GABA B receptors is therefore of great practical importance, for example in the search for new insecticides.

BRIEF SUMMARY OF THE INVENTION

The present invention is therefore based in particular on the object of providing insect GABA B receptors and on assay systems based thereon with a high throughput of test compounds (high throughput screening assays; HTS assays).

BRIEF DESCRIPTION OF THE DRAWINGS

FIG. 1 shows a dose-effect curve of GABA and 3-APMPA on the Drosophila GABA B receptor composed of the polypeptides according to the invention with the amino acid sequences of SEQ ID NO:2 and SEQ ID NO:4, expressed in Xenopus oocytes.

FIG. 2 shows the functional coupling to the intracellular cAMP system of the coexpressed D-GABA B receptors R1/R2 composed of the polypeptides according to the invention with the amino acid sequences of SEQ ID NO:2 and SEQ ID NO:4. HEK293 luc cells which have been stably transfected with D-GABA B R1/R2 (D-GABA R1/2) and untransfected control cells (control) were stimulated with forskolin, forskolin and GABA, and also with GABA alone, and the intracellular cAMP concentration was measured. The D-GABA B-R1/2-transfected cells showed a marked reduction in forskolin-induced cAMP respones, while the control cells were unresponsive.

DETAILED DESCRIPTION OF THE INVENTION

The object is achieved by providing polypeptides which exert at least one biological activity of a GABA B receptor and which comprise an amino acid sequence having at least 70% identity, preferably at least 80% identity, especially preferably at least 90% identity, very especially preferably at least 95% identity, with a sequence of SEQ ID NO: 2, SEQ ID NO: 4 or SEQ ID NO: 6 over a length of at least 20, preferably at least 25, especially preferably at least 30 consecutive amino acids, and very especially preferably over their full lengths.

The degree of identity of the amino acid sequences is preferably determined using the program GAP from the package GCG, Version 9.1, with standard settings (Devereux et al., 1984).

The term "polypeptides" as used in the present context not only relates to short amino acid chains which are usually termed peptides, oligopeptides or oligomers, but also to longer amino acid chains which are usually termed proteins. It encompasses amino acid chains which can be modified either by natural processes, such as post-translational processing, or by chemical prior-art methods. Such modifications may occur at various sites and repeatedly in a polypeptide, such as, for example, on the peptide backbone, on the amino acid side chain, on the amino and/or the carboxyl terminus. For example, they encompass acetylations, acylations, ADP-ribosylations, amidations, covalent linkages to flavins, haem-moieties, nucleotides or nucleotide derivatives, lipids or lipid derivatives or phosphatidylinositol, cyclizations, di-sulphide bridge formations, demethylations, cystine formations, formylations, gamma-carboxylations, glycosylations, hydroxylations, iodinations, methylations, myristylations, oxidations, proteolytic processings, phosphorylations, selenylations and tRNA-mediated amino acid additions.

The polypeptides according to the invention may exist in the form of "mature" proteins or parts of larger proteins, for example as fusion proteins. They can furthermore exhibit secretion or leader sequences, pro-sequences, sequences which allow simple purification, such as multiple histidine residues, or additional stabilizing amino acids.

The biological activity of the GABA B receptors is preferably achieved by hetero-dimerization of the polypeptides according to the invention. For example, the polypeptides according to the invention with an amino acid sequence of SEQ ID NO: 2 and SEQ ID NO: 4, SEQ ID NO: 2 and SEQ ID NO: 6 or SEQ ID NO: 4 and SEQ ID NO: 6 can gain receptor activity by dimerization.

The polypeptides according to the invention need not constitute complete receptors, but may also be fragments thereof, as long as they still have at least one biological activity of the complete receptors. Polypeptides which, compared with GABA B receptors, are composed of the polypeptides according to the invention with an amino acid sequence of SEQ ID NO: 2 and SEQ ID NO: 4, which have a 50% higher or reduced activity, are still considered to be in accordance with the invention. The polypeptides according to the invention need not be deducible from Drosophila melanogaster GABA B receptors. Polypeptides which are also considered as being in accordance with the invention are those which correspond to the GABA B receptors of, for example, the following invertebrates, or fragments thereof which can still exert the biological activity of these receptors: arthropods, nematodes, molluscs.

In comparison with the corresponding region of naturally occurring GABA B receptors, the polypeptides according to the invention can have deletions or amino acid substitutions, as long as they still exert at least one biological activity of the complete receptors, Conservative substitutions are preferred. Such conservative substitutions encompass variations, one amino acid being replaced by another amino acid from amongst the following group:
1. small aliphatic residues, unpolar residues or residues of little polarity: Ala, Ser, Thr, Pro and Gly;
2. polar, negatively charged residues and their amides: Asp, Asn, Glu and Gln;
3. polar, positively charged residues: His, Arg and Lys;
4. large aliphatic unpolar residues: Met, Leu, Ile, Val and Cys; and
5. aromatic residues: Phe, Tyr and Trp.

Preferred conservative substitutions can be seen from the following list:

| Original residue | Substitution |
|---|---|
| Ala | Gly, Ser |
| Arg | Lys |
| Asn | Gln, His |
| Asp | Glu |
| Cys | Ser |
| Gln | Asn |
| Glu | Asp |
| Gly | Ala, Pro |
| His | Asn, Gln |
| Ile | Leu, Val |
| Leu | Ile, Val |
| Lys | Arg, Gln, Glu |
| Met | Leu, Tyr, Ile |
| Phe | Met, Leu, Tyr |
| Ser | Thr |
| Thr | Ser |
| Trp | Tyr |
| Tyr | Trp, Phe |
| Val | Ile, Leu |

The term "biological activity of a GABA B receptor" as used in the present context means binding GABA.

Preferred embodiments of the polypeptides according to the invention are Drosophila melanogaster GABA B receptors which have the amino acid sequence of SEQ ID NO: 2, SEQ ID NO: 4 or SEQ ID NO: 6.

Subject-matter of the present invention are also nucleic acids which encode the polypeptides according to the invention.

The nucleic acids according to the invention are, in particular, single-stranded or double-stranded deoxyribonucleic acids (DNA) or ribonucleic acids (RNA). Preferred embodiments are fragments of genomic DNA which may contain introns, and cDNAs.

cDNAs which have a nucleotide sequence of SEQ ID NO: 1, SEQ ID NO: 3 or SEQ ID NO: 5 constitute preferred embodiments of the nucleic acids according to the invention.

The present invention also encompasses nucleic acids which hybridize under stringent conditions with sequences of SEQ ID NO: 1, SEQ ID NO: 3 or SEQ ID NO: 5.

The term "to hybridize" as used in the present context describes the process during which a single-stranded nucleic acid molecule undergoes base pairing with a complementary strand. Starting from the sequence information disclosed herein, this allows, for example, DNA fragments to be isolated from insects other than Drosophila melanogaster which encode polypeptides with the biological activity of GABA B receptors.

Preferred hybridization conditions are stated hereinbelow:
Hybridization solution: 6×SSC/0% formamide, preferred hybridization solution: 6×SSC/25% formamide
Hybridization temperature: 34° C., preferred hybridization temperature: 42° C.
Wash step 1: 2×SSC at 40° C.,
Wash step 2: 2×SSC at 45° C.; preferred wash step 2: 0.6×SSC at 55° C.,
especially preferred wash step 2: 0.3×SSC at 65° C.

The present invention encompasses furthermore nucleic acids which have at least 70% identity, preferably at least 80% identity, especially preferably at least 90% identity, very especially preferably at least 95% identity, with a sequence of SEQ ID NO: 1, SEQ ID NO: 3 or SEQ ID NO: 5 over a length of at least 20, preferably at least 25, especially preferably at least 30, consecutive nucleotides, and very especially preferably over their full lengths.

The degree of identity of the nucleic acid sequences is preferably determined with the aid of program GAP from the package GCG, Version 9.1, using standard settings.

The sequences in accordance with the GenBank accession numbers (Acc. No.) AC002502, AF145639 and AC004420 are incorporated into the present description by reference.

Subject-matter of the present invention are furthermore DNA constructs which comprise a nucleic acid according to the invention and a heterologous promoter.

The term "heterologous promoter" as used in the present context refers to a promoter which has properties other than the promoter which controls the expression of the gene in question in the original organism. The term "promoter" as used in the present context generally refers to expression control sequences.

The choice of heterologous promoters depends on whether pro- or eukaryotic cells or cell-free systems are used for expression. Examples of heterologous promoters are the SV40, the adenovirus or the cytomegalovirus early or late promoter, the lac system, the trp system, the main operator and promoter regions of phage lambda, the fd coat protein control regions, the 3-phosphoglycerate kinase promoter, the acid phosphatase promoter and the yeast α-mating factor promoter.

Subject-matter of the present invention are furthermore vectors which contain a nucleic acid according to the invention or a DNA construct according to the invention. All the plasmids, phasmids, cosmids, YACs or artificial chromosomes used in molecular biology laboratories can be used as vectors.

Subject-matter of the present invention are also host cells comprising a nucleic acid according to the invention, a DNA construct according to the invention or a vector according to the invention.

The term "host cell" as used in the present context refers to cells which do not naturally comprise the nucleic acids according to the invention.

Suitable host cells are prokaryotic cells such as bacteria from the genera Bacillus, Pseudomonas, Streptomyces, Streptococcus, Staphylococcus, preferably E. coli, but also eukaryotic cells such as yeasts, mammalian cells, amphibian cells, insect cells or plant cells. Preferred eukaryotic host cells are HEK-293, Schneider S2, Spodoptera Sf9, Kc, CHO, COS1, COS7, HeLa, C127, 3T3 or BHK cells and, in particular, Xenopus oocytes.

Another subject-matter of the invention are antibodies which specifically bind to the abovementioned polypeptides or receptors. Such antibodies are produced in the customary manner. For example, such antibodies may be produced by injecting a substantially immunocompetent host with such an amount of a polypeptide according to the invention or a fragment thereof which is effective for antibody production, and subsequently obtaining this antibody. Furthermore, an immortalized cell line which produces monoclonal antibodies may be obtained in a manner known per se. If appropriate, the antibodies may be labelled with a detection reagent. Preferred examples of such a detection reagent are enzymes, radiolabelled elements, fluorescent chemicals or biotin. Instead of the complete antibody, fragments may also be employed which have the desired specific binding properties. The term "antibodies" as used in the present context therefore also extends to parts of complete antibodies, such as Fa, F(ab')$_2$ or Fv fragments, which are still capable of binding to the epitopes of the polypeptides according to the invention.

The nucleic acids according to the invention can be used, in particular, for generating transgenic invertebrates. These may be employed in assay systems which are based on an expression, of the polypeptides according to the invention, which deviates from the wild type. Based on the information disclosed herein, it is furthermore possible to generate transgenic invertebrates where expression of the polypeptides according to the invention is altered owing to the modification of other genes or promoters.

The transgenic invertebrates are generated, for example, in the case of Drosophila melanogaster, by P-element-mediated gene transfer (Hay et al., 1997), or, in Caenorhabditis elegans, by transposon-mediated gene transfer (for example by Tcl; Plasterk, 1996).

Subject-matter of the invention are therefore also transgenic invertebrates which contain at least one of the nucleic acids according to the invention, preferably transgenic invertebrates of the species Drosophila melanogaster or Caenorhabditis elegans, and their transgenic progeny. The transgenic invertebrates preferably contain the polypeptides according to the invention in a form which deviates from the wild type.

Subject-matter of the present invention are furthermore processes for producing the polypeptides according to the invention. To produce the polypeptides encoded by the nucleic acids according to the invention, host cells which contain one of the nucleic acids according to the invention can be cultured under suitable conditions, where the nucleic acid to be expressed may be adapted to the codon usage of the host cells. Thereupon, the desired polypeptides can be isolated from the cells or the culture medium in the customary manner. The polypeptides may also be produced in in vitro systems.

A rapid method of isolating the polypeptides according to the invention which are synthesized by host cells using a nucleic acid according to the invention starts with the expression of a fusion protein, it being possible for the fusion partner to be affinity-purified in a simple manner. For example, the fusion partner may be glutathione S-transferase. The fusion protein can then be purified on a glutathione affinity column. The fusion partner can then be removed by partial proteolytic cleavage, for example at linkers between the fusion partner and the polypeptide according to the invention to be purified. The linker can be designed such that it includes target amino acids such as arginine and lysine residues, which define sites for trypsin cleavage. To generate such linkers, standard cloning methods using oligonucleotides may be employed.

Other purification methods which are possible are based on preparative electrophoresis, FPLC, HPLC (for example using gel filtration, reversed-phase or moderately hydrophobic columns), gel filtration, differential precipitation, ion-exchange chromatography and affinity chromatography.

Since GABA B receptors constitute membrane proteins, the purification methods preferably involve detergent extractions, for example using detergents which have no, or little, effect on the secondary and tertiary structures of the polypeptides, such as nonionic detergents.

The purification of the polypeptides according to the invention can encompass the isolation of membranes, starting from host cells which express the nucleic acids according to the invention. Such cells preferably express the polypeptides according to the invention in a sufficiently high copy number, so that the polypeptide quantity in a membrane fraction is at least 10 times higher than that in comparable membranes of cells which naturally express GABA B receptors; especially preferably, the quantity is at least 100 times, very especially preferably at least 1000 times higher.

The terms "isolation or purification" as used in the present context mean that the polypeptides according to the invention are separated from other proteins or other macromolecules of the cell or of the tissue. The protein content of a composition containing the polypeptides according to the invention is preferably at least 10 times, especially preferably at least 100 times, higher than in a host cell preparation.

The polypeptides according to the invention may also be affinity-purified without a fusion partner with the aid of antibodies which bind to the polypeptides.

Another subject-matter of the present invention are processes for the generation of the nucleic acids according to the invention. The nucleic acids according to the invention can be generated in the customary manner. For example, all of the nucleic acid molecules can be synthesized chemically, or else only short sections of the sequences according to the invention can be synthesized chemically, and such oligonucleotides can be radiolabelled or labelled with a fluorescent dye. The labelled oligonucleotides can be used for screening cDNA libraries generated starting from insect mRNA or for screening genomic libraries generated starting from insect genomic DNA. Clones which hybridize with the labelled oligonucleotides are chosen for isolating the DNA in question. After characterization of the DNA which has been isolated, the nucleic acids according to the invention are obtained in a simple manner.

Alternatively, the nucleic acids according to the invention can also be generated by means of PCR methods using chemically synthesized oligonucleotides.

The term "oligonucleotide(s)" as used in the present context denotes DNA molecules composed of 10 to 50 nucleotides, preferably 15 to 30 nucleotides. They are synthesized chemically and can be used as probes.

The nucleic acids or polypeptides according to the invention allow new active compounds for crop protection and/or pharmaceutical active compounds for the treatment of humans and animals to be identified, such as chemical compounds which, being modulators, in particular agonists or antagonists, alter the properties of the GABA B receptors according to the invention. To this end, a recombinant DNA molecule comprising at least one nucleic acid according to the invention is introduced into a suitable host cell. The host cell is grown in the presence of a compound or a sample comprising a variety of compounds under conditions which allow expression of the receptors according to the invention. A change in the receptor properties can be detected for example as described hereinbelow in Example 2. This allows, for example, insecticidal substances to be found.

GABA B receptors alter the concentration of intracellular cAMP via interaction with G proteins, preferably after previously having been activated. Thus, changes in the receptor properties by chemical compounds can be measured after heterologous expression, for example by measuring the intracellular cAMP concentrations directly via ELISA assay systems (Biomol, Hamburg, Germany) or RIA assay systems (NEN, Schwalbach, Germany) in HTS format. An indirect measurement of the cAMP concentration is possible with the aid of reporter genes (for example luciferase), whose expression depends on the cAMP concentration (Stratowa et al., 1995). The coexpression of GABA B receptors with specific G proteins, for example G$\alpha$15, G$\alpha$15 or else chimeric G proteins, in heterologous systems and measuring the rise in calcium, for example using fluorescent dyes or equorin, is an alternative possibility of carrying out the screening (Stables et al., 1997; Conklin et al., 1993).

Furthermore, the binding of GTP to the activated G protein can be used as a read-out-system for assaying substances. Also, binding experiments with labelled GABA can be employed for screening.

The term "agonist" as used in the present context refers to a molecule which activates GABA B receptors.

The term "antagonist" as used in the present context refers to a molecule which displaces an agonist from its binding site.

The term "modulator" as used in the present invention constitutes the generic term for agonist and antagonist. Modulators can be small organochemical molecules, peptides or antibodies which bind to the polypeptides according to the invention. Other modulators may be small organochemical molecules, peptides or antibodies which bind to a molecule which, in turn, binds to the polypeptides according to the invention, thus affecting their biological activity. Modulators may constitute mimetics of natural substrates and ligands.

The modulators are preferably small organochemical compounds.

The binding of the modulators to the polypeptides according to the invention can alter the cellular processes in a manner which leads to the death of the insects treated therewith.

The present invention therefore also extends to the use of modulators of the poly-peptides according to the invention as insecticides.

The nucleic acids or polypeptides according to the invention also allow compounds to be found which bind to the receptors according to the invention. Again, they can be applied to plants as insecticides. For example, host cells which contain the nucleic acids according to the invention and which express the corresponding receptors or polypeptides, or the gene products themselves, are brought into contact with a compound or a mixture of compounds under conditions which permit the interaction of at least one compound with the host cells, the receptors or the individual poly-peptides.

Using host cells or transgenic invertebrates which contain the nucleic acids according to the invention, it is also possible to find substances which alter receptor expression.

The above-described nucleic acids according to the invention, vectors and regulatory regions can furthermore be used for finding genes which encode polypeptides which participate in the synthesis, in insects, of functionally similar GABA B receptors. Functionally similar receptors are to be understood as meaning in accordance with the present invention receptors which comprise polypeptides which, while differing from the amino acid sequence of the polypeptides described herein, essentially have the same functions.

Information on the Sequence Listing and the Figures

SEQ ID NO: 1, SEQ ID NO: 3 and SEQ ID NO: 5 show the nucleotide and amino acid sequences of the isolated GABA B cDNAs. SEQ ID NO: 2, SEQ ID NO: 4 and SEQ ID NO: 6 furthermore show the amino acid sequences of the proteins deduced from the GABA B cDNA sequences.

FIG. 1 shows a dose-effect curve of GABA and 3-APMPA on the Drosophila GABA B receptor composed of the polypeptides according to the invention with the amino acid sequences of SEQ ID NO: 2 and SEQ ID NO: 4, expressed in Xenopus oocytes.

FIG. 2 shows the functional coupling to the intracellular cAMP system of the coexpressed D-GABA B receptors R1/R2 composed of the polypeptides according to the invention with the amino acid sequences of SEQ ID NO: 2 and SEQ ID NO: 4. HEK293 luc cells which have been stably transfected with D-GABA B R1/R2 (D-GABA R1/2) and untransfected control cells (control) were stimulated with forskolin, forskolin and GABA, and also with GABA alone, and the intracellular cAMP concentration was measured. The D-GABA B-R1/2-transfected cells showed a marked reduction in forskolin-induced cAMP response, while the control cells were unresponsive.

EXAMPLES

Example 1

Isolation of the above-described polynucleotide sequences

Polynucleotides were manipulated by standard methods of recombinant DNA technology (Sambrook et al., 1989). Nucleotide and protein sequences were processed in terms of bioinformatics using the package GCG Version 9.1 (GCG Genetics Computer Group, Inc., Madison Wis., USA).

Example 2

Generation of the Expression Constructs

The sequence regions of SEQ ID NO: 1, SEQ ID NO: 3 and SEQ ID NO: 5 were amplified by means of polymerase chain reaction (PCR) and cloned into the vector pcDNA3.1/Neo (Invitrogen, Groningen).

Heterololous Expression

HEK293 cells were cultured at 5% $CO_2$ and 37° C. in Dulbecco's modified Eagle's medium and 10% foetal calf serum. MBS (Stratagene, La Jolla, USA) was used for the gene transfer, following the manufacturer's instructions. 24 h to 48 h after the gene transfer, the cells were sown intro microtiter plates at various densities. Recombinant cells were selected over 3 to 4 weeks by growth in Dulbecco's modified Eagles medium and 10% foetal calf serum and 700 µg/ml Geneticin (G418, Life Technologies, Karlsruhe) as selection marker. Individual resistant clones were analysed as described below.

Insect GABA B receptors were also expressed functionally in Xenopus oocytes. To this end, G-protein-activatable potassium channels (GIRK1 and GIRK4) were coexpressed in order to measure activation of the GABA B receptors (White et al., 1998).

cAMP Measurements

HEK293 cell strains were used for determining the cAMP concentration. On the one hand, HEK293 cells stably coexpressed the two Drosophila melanogaster receptors D-GABA B R1 and D-GABA B R2 (D-GABA R1/2). On the other hand, untransfected control cells were incorporated into the assay (control). In each case, the cells were plated into 96-well-plates at a density of 20,000 cells per cavity. Control cells were incubated in culture medium (DMEM, 10% FCS, penicillin and streptomycin, 50 U/ml and 50 µg/ml (Life Technologies)) and D-GABA-R1/2 expressing cells in selection medium (culture medium with 0.5 mg/ml Geneticin (G418, Life Technologies)) for 48 hours at 37° C. until a cell density of approximately 80% was reached. Thereupon, the medium was removed, and the cells were washed once with unsupplemented DMEM. After incubation for 30 minutes with IBMX (300 µM) at 37° C., cells were stimulated for 30 minutes with GABA (100 µM) and/or forskolin (10 µM) at 37° C. All incubation steps were carried out in unsupplemented DMEM (Life Technologies). Then, the stimulation medium was removed and the cells were lysed with 50 µl of HCl (0.1 N) per cavity. The cells were lysed for 20 minutes at room temperature with shaking, and the cAMP concentration of the cell lysates were determined in triplicate using the enzyme immunoassay (EIA) kit AK-200 (Biomol, Hamburg, Germany) following the manufacturer's description.

Oocyte Measurements

1. Oocyte Preparation

The oocytes were obtained from an adult female Xenopus laevis frog (Horst Kahler, Hamburg, Germany). The frogs were kept in large tanks with circulating water at a water temperature of 20–24° C. Parts of the frog ovary were removed through a small incision in the abdomen (approx. 1 cm), with full anaesthesia. The ovary was then treated for approximately 140 minutes with 25 ml collagenase (type I, C-0130, SIGMA-ALDRICH CHEMIE GmbH, Deisenhofen, Germany; 355 U/ml, prepared with Barth's solution without calcium in mM: NaCl 88, KCl 1, $MgSO_4$ 0.82, $NaHCO_3$ 2.4, Tris/HCl 5, pH7.4), with constant shaking. Then, the oocytes were washed with Barth's solution without calcium. Only oocytes at maturity stage V (Dumont, 1972) were selected for the further treatment and transferred into microtiter plates (Nunc MicroWell™ plates, cat. No. 245128+263339 (lid), Nunc GmbH & Co. KG, Wiesbaden, Germany) filled with Barth's solution (in mM: NaCl 88, KCl 1, $MgSO_4$ 0.82, $Ca(NO_3)_2$ 0.33, $CaCl_2$ 0.41, $NaHCO_3$ 2.4, Tris/HCl 5, pH7.4) and gentamicin (gentamicin sulphate, G-3632, SIGMA-ALDRICH CHEMIE GmbH, Deisenhofen, Germany; 100 U/ml). Then, the oocytes were kept in a cooling incubator (type KB 53, WTB Binder Labortechnik GmbH, Tuttlingen, Germany) at 19.2° C.

2. Injecting the Oocytes

Injection electrodes of diameter 10–15 µm were prepared using a pipette-drawing device (type L/M-3P-A, List-electronic, Darmstadt-Eberstadt, Germany). Prior to injection, aliquots with the D-GABA B DNA or GIRK1/4 DNA were defrosted and diluted with water to a final concentration of 10 ng/µl. The DNA samples were centrifuged for 120 seconds at 3200 g (type Biofuge 13, Heraeus Instruments GmbH, Hanau, Germany). An extended PE tube was subsequently used as transfer tube to fill the pipettes from the rear end. The injection electrodes were attached to a X,Y,Z positioning system (treatment centre EP1090, isel-automation, Eiterfeld, Germany). With the aid of a Macintosh computer, the oocytes in the microtiter plate wells were approached, and approximately 50 nl of the DNA solution were injected into the oocytes by briefly applying a pressure (0.5–3.0 bar, 3–6 seconds).

3. Electrophysiological Measurements

A two-electrode voltage terminal equipped with a TURBO TEC-10CD (npi electronic GmbH, Tamm, Germany) amplifier was used to carry out the electrophysiological measurements. The micropipettes required for this purpose were drawn in two movements from aluminium silicate glass (capillary tube, Article No. 1463029, 1=100 mm, $Ø_{ext.}$=1.60 mm, $Ø_{int.}$=1.22 mm, Hilgenberg GmbH, Malsfeld, Germany) (Hamill et al., 1981). Current and voltage electrodes had a diameter of 1–3 µm and were filled with 1.5 M KCl and 1.5 M potassium acetate. The pipettes had a capacitance of 0.2–0.5 MW. To carry out the electrophysiological measurements, the oocytes were transferred into a small chamber which was flushed continuously with normal Rimland solution (in mM: KCl 90, $MgCl_2$ 3, HEPES 5, pH 7.2). To apply a substance, the perfusion solution was exchanged for a substance solution with the same composition and additionally the desired substance concentration. The successful expression of the D-GABA B DNA was checked after one week at a terminal potential of −60 mV. Unresponsive oocytes were discarded. All the others were used for substance testing. The data were documented by means of a YT plotter (YT plotter, Model BD 111, Kipp & Zonen Delfl BV, AM Delft, Netherlands). When test substances were assayed in concentration series, these measurements were carried out on at least two different oocytes and at at least five different concentrations. The substances have been assayed directly without preincubation in the presence of GABA (gamma-amino-N-butyric acid, A2129, SIGMA-ALDRICH CHEMIE GmbH, Deisenhofen, Germany) for their antagonism. The individual data were entered in Origin (evaluation software Microcal Origin, Microcal Software, Inc., Northampton, Mass. 01060-4410 USA) (Additive GmbH, Friedrichsdorf/Ts, Germany). Means, standard deviation, $IC_{50}$ values and $IC_{50}$ curves were calculated using Origin. These measurements were carried out at least in duplicate.

References

Conklin et al. (1993) Substitution of three amino acids switches receptor specificity of Gq alpha to that of Gi alpha, Nature 363, 274–276

Devereux et al. (1984) Nucleic Acids Research 12, 387

Dumont, J. N. (1972) Oogenesis in *Xenopus laevis* (Daudin). 1. Stages of oocyte development in laboratory maintained animals, J. Morphol. 136, 153–180

Fukunaga, A. et al. (1999) Insecticidal properties of 3-aminopropyl(methyl)-phosphinic acid and its effect on K+-evoked release of acetylcholine from cockroach synaptosomes, Comp. Biochem. and Pysiol. Part C 122, 283–286 ffrench-Constant, R. H. et al. (1991) Molecular cloning and transformation of cyclodiene resistance in Drosophila: an invertebrate gamma-aminobutyric acid subtype A receptor locus, Proc. Natl. Acad. Sci. U.S.A. 88, 7209–7213

Hamill, O. P. et al. (1981) Improved patch-clamp techniques for high-resolution current recording from cells and cell-free membrane patches, Pfügers Arch. 391, 85–100

Harvey, R. J. et al. (1994) Sequence of a Drosophila ligand-gated ion-channel polypeptide with an unusual amino-terminal extracellular domain, J. Neurochem. 62, 2480–2483

Hay et al. (1997) P element insertion-dependent gene activation in the Drosophila eye, Proceedings of The National Academy of Sciences of The United States of America 94 (10), 5195–5200

Henderson, J. E. et al. (1993) Characterization of a putative gamma-aminobutyric acid (GABA) receptor beta subunit gene from Drosophila melanogaster, Biochem. Biophys. Res. Commun. 193, 474–482

Jones K. A. et al. (1998) GABA(B) receptors function as a heteromeric assembly of the subunits GABA(B)R1 and GABA(B)R2, Nature 396, 674–679

Kaupmann K. et al. (1998) GABA(B)-receptor subtypes assemble into functional heteromeric complexes, Nature 396, 683–687

Plasterk (1996) The Tc1/mariner transposon family, Transposable Elements/Current Topics in Microbiology and Immunology 204, 125–143

Sambrook et al. (1989) Molecular Cloning, A Laboratory Manual, 2nd ed. Cold Spring Harbour Press Sattelle D. B. (1990) GABA Receptors of Insects, Advances in Insect Physiology 22, 1–113

Stables et al. (1997) A Bioluminescent Assay for Agonist Activity at Potentially Any G-protein coupled Receptor, Analytical Biochemistry 252, 115–126

Stratowa C. et al. (1995) Use of a luciferase reporter system for characterizing G-protein-linked receptors, Current Opinion in Biotechnology 6, 574–581

---

What is claimed is:

1. A method of identifying a chemical which specifically binds to a polypeptide, the method comprising:

exposing to at least one chemical under conditions permitting interaction therewith a polypeptide comprising an amino acid sequence of SEQ ID NO:2; and identifying the chemical specifically binding to the polypeptide, wherein the polypeptide has at least one biological activity of a GABA B receptor.

* * * * *